US007939519B2

(12) United States Patent
Pan et al.

(10) Patent No.: US 7,939,519 B2
(45) Date of Patent: May 10, 2011

(54) IMMUNOSUPPRESANT COMPOUNDS AND COMPOSITIONS

(75) Inventors: Shifeng Pan, San Diego, CA (US); Wenqi Gao, San Diego, CA (US); Nathanael S Gray, San Diego, CA (US); Yuan Mi, San Diego, CA (US); Yi Fan, Poway, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/024,992

(22) Filed: Feb. 1, 2008

(65) Prior Publication Data

US 2009/0036423 A1    Feb. 5, 2009

Related U.S. Application Data

(63) Continuation of application No. 10/849,323, filed on May 19, 2004, now abandoned.

(60) Provisional application No. 60/471,931, filed on May 19, 2003, provisional application No. 60/561,968, filed on Apr. 14, 2004.

(51) Int. Cl.
A61K 31/397 (2006.01)
C07D 205/00 (2006.01)

(52) U.S. Cl. .................................. 514/210.17; 548/953

(58) Field of Classification Search .................. None
See application file for complete search history.

(56) References Cited

U.S. PATENT DOCUMENTS

| 3,697,513 | A | 10/1972 | Siegrist .......................... 260/240 |
| 5,506,240 | A | 4/1996 | Schmidlin et al. |
| 5,620,998 | A | 4/1997 | Schmidlin et al. |
| 5,955,487 | A | 9/1999 | Schmidlin et al. |
| 6,127,408 | A | 10/2000 | Kelleher et al. ............... 514/471 |
| 6,423,508 | B1 | 7/2002 | Bergsma et al. ............. 435/69.1 |
| 2005/0033055 | A1 | 2/2005 | Bugianesi et al. |

FOREIGN PATENT DOCUMENTS

| EP | 0 635 492 | 7/1994 |
| EP | 1002792 | 5/2000 |
| EP | 1050301 | 11/2000 |
| EP | 1 380 562 A1 | 4/2002 |
| EP | 1 201 648 A1 | 5/2002 |
| EP | WO 02/092068 | 11/2002 |
| EP | 1 391 199 A1 | 2/2004 |
| EP | 1430894 | 6/2004 |
| EP | 1 553 075 A1 | 7/2005 |
| EP | 1 661 881 A2 | 5/2006 |
| GB | 1 379 533 | 1/1975 |
| JP | 8-188564 | 7/1996 |
| JP | 11-500745 | 1/1999 |
| JP | 2000-502343 | 2/2000 |
| JP | 2000-502354 | 2/2000 |
| JP | 2001-151771 | 6/2001 |
| JP | 2002-167371 | 6/2002 |
| JP | 2002-531539 | 9/2002 |
| JP | 2002-541109 | 12/2002 |
| JP | 2003-73357 | 3/2003 |
| JP | 2003-587782 | 9/2003 |
| JP | 2005-528348 | 9/2003 |
| JP | 2005-527612 | 9/2005 |
| JP | 2006-517591 | 7/2006 |
| JP | 2006-528698 | 12/2006 |
| WO | WO94/22863 | 10/1994 |
| WO | WO96/05828 | 2/1996 |
| WO | WO 97/13759 | 4/1997 |
| WO | WO 97124119 | 7/1997 |
| WO | WO 00/59510 | 10/2000 |
| WO | WO 01/10825 | 2/2001 |
| WO | WO02/18395 | 3/2002 |
| WO | WO 02/055501 | 7/2002 |
| WO | WO 02/100812 | 12/2002 |
| WO | WO03/018578 | 3/2003 |
| WO | WO03/037271 | 5/2003 |
| WO | 03/061567 | 7/2003 |
| WO | WO03/007405 | 9/2003 |
| WO | 03/091219 | 11/2003 |
| WO | WO 03/091219 | 11/2003 |
| WO | 2004/014856 | 2/2004 |
| WO | WO 2004/031118 | 4/2004 |
| WO | WO 2005/000833 A1 | 1/2005 |
| WO | WO 2005/020882 | 3/2005 |

OTHER PUBLICATIONS

Chawla et al., "Challenges in Polymorphism of Pharmaceuticals", CRIPS vol. 5, No. 1, Jan.-Mar. 2004 (4 Pages.*
Newman et al., "Solid-state analysis of the active pharmaceutical ingredient in drug products", DDT vol. 8, No. 19, Oct. 2003, p. 898-905.*
Database Caplus on STN, Accession No. 2001: 115110, Ozaki et al., "Preparation of Carbamate derivatives as agricultural or horticultural bactericides", Feb. 15, 2001, see abstract and RN 325155-48-4P.
Smith, C.D. et al., "Electrospray mass spectrometry of stable iminyl nitroxide and nitronyl nitroxide free radicals", Journal of Mass Spectrometry, 2002, vol. 37, No. 9, pp. 897-902.
Database CA, Fisher, Matthew J. et al., "Dihydroisoquinolone RGD mimics. Exploration of the aspartate isostere", XP002504798, (1997).
Vachal et al., "Highly Selective and Potent Agonists of Sphingosine-1-phosphate 1 (S1P1) Receptor", Bioorganic & Medicinal Chemistry Letters, 16 (2006) 3684-3687.
Yan et al., "Discovery of 3-arylpropionic acids as potent agonists of sphingosine-1-phosphate receptor-1 (S1P1) with-high selectivity against all other known S1P receptor subtypes", Biorganic & Medicinal Chemistry Letters, 16 (2006), 3679-3683.
Li et al., "Discovery of Potent 3, 5-Diphenyl-1,2,4-oxadiazole Sphingosine-1-phosphate-1-phosphate-1 (S1 P1) Receptro Agonists with Exceptional Selectivity agains S1P2 and S1P3", Journal of Medicinal Chemistry, 2005, 48, 20, p. 6169-6173.
Pan et.al., caplus AN 2005:977010 "Preparation of 5-(benzyloxyimino)-5,6,7,8-tetrahydronaphthalen-2-ylmethylamines as immunosuppressants", (2007).

(Continued)

Primary Examiner — Sun Jae Y. Loewe
(74) Attorney, Agent, or Firm — Karen DeBenedictis; Jennifer Chin Chapman; Cozette M. McAvoy

(57) ABSTRACT

The present invention relates to immunosuppressant, process for their production, their uses and pharmaceutical compositions containing them. The invention provides a novel class of compounds useful in the treatment or prevention of diseases or disorders mediated by lymphocyte interactions, particularly diseases associated with EDG receptor mediated signal transduction.

2 Claims, No Drawings

OTHER PUBLICATIONS

Ghosh, et al: "Preparation of compounds as C-C chemokine receptor 8 antagonists, pharmaceutical compositions and use agent inflammatory or viral disorders", abstract of W02003-0337271, XP-002983911.

Maskovskij M.D.: "Medicaments", Moscow, 1993, part 1, p. 8.

"Chemical encyclopaedic dictionary", Moscow, "Sovjetskaja Encyclopaedia", 1983, pp. 130-131.

Alexejev V. V. "Optical isometry and pharmacological activity of medical preparations", Sorovskij obrasovatel'nyj zurnal, 1998, No. 1.

M. D. Maskovskij, "Medicaments", vol. 2001, p. 11.

Reinharrd et al., Neuroleptic Activity of Chiral *trans*-Hexahydro-γ-carbolines, Journal of Medicinal Chemistry, vol. 29 (1), pp. 8-19, (1986).

Son-ichi et at., "Ruthenium-Catalyzed Oxidation of Amides and Lactams with Peroxides," J. Am. Chem. Soc., Pet. vol. 112(21), pp. 7820-7822, (1990).

Chau et al., "Convergent Synthesis of Naphthylisoquinoline Alkaloids: Total Synthesis of (+)-O-Methylancistrocline," J. Org. Chem., vol. 61 (20), pp. 7101-7105, (1996).

Chiusoli et al.,"Palladium-Catalyzed Carbonylation of Alkynes, IV. (*)Trapping of Cyclopentadienones by Dienophiles, ()(*)," Gazzetta Chimica Italiana, vol. 117 (11), pp. 695-700, (1987), (English).

Maskovskij, M. D., "Medicaments," vol. 16, pp. 452-463, (1981).

* cited by examiner

IMMUNOSUPPRESANT COMPOUNDS AND COMPOSITIONS

CROSS-REFERENCE TO RELATED APPLICATIONS

This application claims the benefit of priority to U.S. Provisional Patent Application No. 60/471,931 (filed 19 May 2003) and U.S. Provisional Patent Application No. 60/561,968 (filed 14 Apr. 2004). The full disclosures of these applications are incorporated herein by reference in their entirety and for all purposes.

BACKGROUND OF THE INVENTION

1. Field of the Invention

The invention provides a novel class of immunosuppressant compounds useful in the treatment or prevention of diseases or disorders mediated by lymphocyte interactions, particularly diseases associated with EDG receptor mediated signal transduction.

2. Background

EDG receptors belong to a family of closely related, lipid activated G-protein coupled receptors. EDG-1, EDG-3, EDG-5, EDG-6, and EDG-8 (also respectively termed S1P1, S1P3, S1P2, S1P4, and S1P5) are identified as receptors specific for sphingosine-1-phosphate (S1P). EDG2, EDG4, and EDG7 (also termed LPA1, LPA2, and LPA3, respectively) are receptors specific for lysophosphatidic (LPA). Among the S1P receptor isotypes, EDG-1, EDG-3 and EDG-5 are widely expressed in various tissues, whereas the expression of EDG-6 is confined largely to lymphoid tissues and platelets, and that of EDG-8 to the central nervous system. EDG receptors are responsible for signal transduction and are thought to play an important role in cell processes involving cell development, proliferation, maintenance, migration, differentiation, plasticity and apoptosis. Certain EDG receptors are associated with diseases mediated by lymphocyte interactions, for example, in transplantation rejection, autoimmune diseases, inflammatory diseases, infectious diseases and cancer. An alteration in EDG receptor activity contributes to the pathology and/or symptomology of these diseases. Accordingly, molecules that themselves alter the activity of EDG receptors are useful as therapeutic agents in the treatment of such diseases.

SUMMARY OF THE INVENTION

This application relates to compounds selected from Formula Ia and Ib:

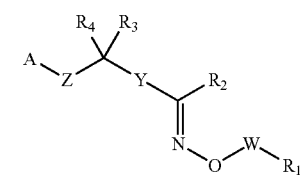

Ia

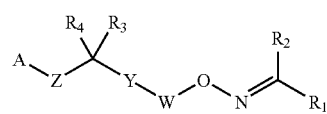

Ib in which:

A is chosen from $-C(O)OR_5$, $-OP(O)(OR_5)_2$, $-P(O)(OR_5)_2$, $-S(O)_2OR_5$, $-P(O)(R_5)OR_5$ and 1H-tetrazol-5-yl; wherein each $R_5$ is independently chosen from hydrogen and $C_{1-6}$alkyl;

W is chosen from a bond, $C_{1-3}$alkylene, $C_{2-3}$alkenylene;

Y is chosen from $C_{6-10}$aryl and $C_{2-9}$heteroaryl; wherein any aryl or heteroaryl of Y can be optionally substituted with 1 to 3 radicals chosen from halo, hydroxy, nitro, $C_{1-6}$alkyl, $C_{1-6}$alkoxy, halo-substituted $C_{1-6}$alkyl and halo-substituted $C_{1-6}$alkoxy;

Z is chosen from:

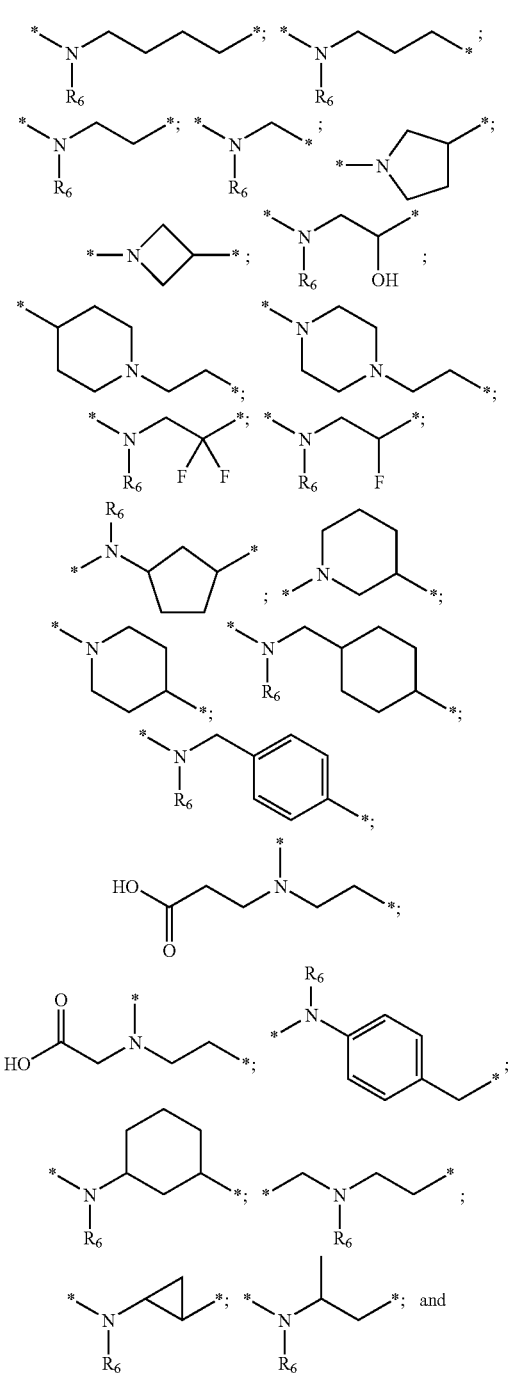

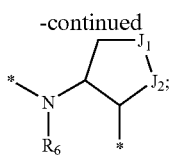

wherein the left and right asterisks of Z indicate the point of attachment between —C(R$_3$)(R$_4$) and A of Formula Ia or Ib, respectively; R$_6$ is chosen from hydrogen and C$_{1-6}$alkyl; and J$_1$ and J$_2$ are independently methylene or a heteroatom chosen from S, O and NR$_5$; wherein R$_5$ is chosen from hydrogen and C$_{1-6}$alkyl; and any alkylene of Z can be further substituted by one to three radicals chosen from halo, hydroxy, C$_{1-6}$alkyl; or R$_6$ can be attached to a carbon atom of Y to form a 5-7 member ring;

R$_1$ is chosen from C$_{6-10}$aryl and C$_{2-9}$heteroaryl; wherein any aryl or heteroaryl of R$_1$ is optionally substituted by a radical chosen from C$_{6-10}$arylC$_{0-4}$alkyl, C$_{2-9}$heteroarylC$_{0-4}$alkyl, C$_{3-8}$cycloalkylC$_{0-4}$alkyl, C$_{3-8}$heterocloalkylC$_{0-4}$alkyl or C$_{1-6}$alkyl; wherein any aryl, heteroaryl, cycloalkyl or heterocycloalkyl group of R$_1$ can be optionally substituted by one to five radicals chosen from halo, C$_{1-6}$alkyl, C$_{1-6}$alkoxy, halo-substituted-C$_{1-6}$alkyl and halo-substituted-C$_{1-6}$alkoxy; and any alkyl group of R$_1$ can optionally have a methylene replaced by an atom or group chosen from —S—, —S(O)—, —S(O)$_2$—, —NR$_5$— and —O—; wherein R$_5$ is chosen from hydrogen or C$_{1-6}$alkyl;

R$_2$ is chosen from hydrogen, C$_{1-6}$alkyl, C$_{2-6}$alkenyl, C$_{2-6}$alynyl and halo substituted C$_{1-6}$alkyl;

R$_3$ and R$_4$ are independently chosen from hydrogen, C$_{1-6}$alkyl, halo, hydroxy, C$_{1-6}$alkoxy, halo-substituted C$_{1-6}$alkyl and halo-substituted C$_{1-6}$alkoxy; and the N-oxide derivatives, prodrug derivatives, protected derivatives, individual isomers and mixtures of isomers thereof; and the pharmaceutically acceptable salts and solvates (e.g. hydrates) of such compounds.

A second aspect of the invention is a pharmaceutical composition which contains a compound of Formula Ia or Ib or an N-oxide derivative, individual isomer or mixture of isomers thereof, or a pharmaceutically acceptable salt thereof, in admixture with one or more suitable excipients.

A third aspect of the invention is a method for treating a disease in an animal in which alteration of EDG receptor mediated signal transduction can prevent, inhibit or ameliorate the pathology and/or symptomology of the disease, which method comprises administering to the animal a therapeutically effective amount of a compound of Formula Ia or Ib or a N-oxide derivative, individual isomer or mixture of isomers thereof; or a pharmaceutically acceptable salt thereof.

A fourth aspect of the invention is the use of a compound of Formula Ia or Ib in the manufacture of a medicament for treating a disease in an animal in which alteration of EDG receptor mediated signal transduction contributes to the pathology and/or symptomology of the disease.

A fifth aspect of the invention is a process for preparing compounds of Formula Ia or Ib and the N-oxide derivatives, prodrug derivatives, protected derivatives, individual isomers and mixtures of isomers thereof; and the pharmaceutically acceptable salts thereof.

DESCRIPTION OF THE PREFERRED EMBODIMENTS

The invention provides compounds that are useful in the treatment and/or prevention of diseases or disorders mediated by lymphocyte interactions. Also provided are methods for treating such diseases or disorders.

DEFINITIONS

In this specification, unless otherwise defined:

"Alkyl" as a group and as a structural element of other groups, for example halo-substituted-alkyl, alkoxy, acyl, alkylthio, alkylsulfonyl and alkylsulfinyl, can be either straight-chained or branched. "Alkenyl" as a group and as a structural element of other groups contains one or more carbon-carbon double bonds, and can be either straight-chain, or branched. Any double bonds can be in the cis- or trans-configuration. "Alkynyl" as a group and as structural element of other groups and compounds contains at least one C≡C triple bond and can also contain one or more C═C double bonds, and can, so far as possible, be either straight-chain or branched. Any cycloalkyl group, alone or as a structural element of other groups can contain from 3 to 8 carbon atoms, preferably from 3 to 6 carbon atoms. "Alkylene" and "alkenylene" are divalent radicals derived from "alkyl" and "alkenyl" groups, respectively. In this application, any alkyl group of R$^1$ can be optionally interrupted by a member of the group selected from —S—, —S(O), —S(O)$_2$—, —NR$^{20}$— and —O— (wherein R$^{20}$ is hydrogen or C$_{1-6}$alkyl). These groups include —CH$_2$—O—CH$_2$—, —CH$_2$—S(O)$_2$—CH$_2$—, —(CH$_2$)$_2$—NR$^2$—CH$_2$—, —CH$_2$—O(CH$_2$)$_2$—, and the like.

"Aryl" means a monocyclic or fused bicyclic aromatic ring assembly containing six to ten ring carbon atoms. For example, C$_{6-12}$aryl can be phenyl, biphenyl or naphthyl, preferably phenyl. A fused bicyclic ring can be partially saturated, for example, 1,2,3,4-tetrahydro-naphthalene, and the like. "Arylene" means a divalent radical derived from an aryl group. For example, arylene as used in this application can be phenylene, biphenylene, naphthylene and the like.

"Halo" or "halogen" means F, Cl, Br or I, preferably F or Cl. Halo-substituted alkyl groups and compounds can be partially halogenated or perhalogenated, whereby in the case of multiple halogenation, the halogen substituents can be identical or different. A preferred perhalogenated alkyl group is for example trifluoromethyl or trifluoromethoxy.

"Heteroaryl" means aryl, as defined in this application, with the addition of at least one heteroatom moiety selected from N, O or S, and each ring is comprised of 5 to 6 ring atoms, unless otherwise stated. For example, C$_2$heteroaryl includes oxadiazole, triazole, and the like. C$_9$heteroaryl includes quinoline, 1,2,3,4-tetrahydro-quinoline, and the like. C$_{2-9}$heteroaryl as used in this application includes thienyl, pyridinyl, furanyl, isoxazolyl, benzoxazolyl or benzo[1,3]dioxolyl, preferably thienyl, furanyl or pyridinyl. "Heteroarylene" means heteroaryl, as defined in this application, provided that the ring assembly comprises a divalent radical. A fused bicyclic heteroaryl ring system can be partially saturated, for example, 2,3-dihydro-1H-isoindole, 1,2,3,4-tetrahydro-quinoline, and the like.

As used in the present invention, an EDG-1 selective compound (agent or modulator) has a specificity that is selective for EDG-1 over EDG-3 and over one or more of EDG-5, EDG-6, and EDG-8. As used herein, selectivity for one EDG receptor (a "selective receptor") over another EDG receptor (a "non-selective receptor") means that the compound has a much higher potency in inducing activities mediated by the selective EDG receptor (e.g., EDG-1) than that for the non-selective S1P-specific EDG receptor. If measured in a GTP-γS binding assay (as described in the Example below), an EDG-1 selective compound typically has an EC50 (effective concentration that causes 50% of the maximum response) for a selective receptor (EDG-1) that is at least 5, 10, 25, 50, 100, 500, or 1000 fold lower than its EC50 for a non-selective receptor (e.g., one or more of EDG-3, EDG-5, EDG-6, and EDG-8).

DETAILED DESCRIPTION OF THE INVENTION

The invention provides compounds that are useful for treating or preventing diseases or disorders that are mediated by lymphocyte interactions. In one embodiment, for compounds of Formula Ia or Ib, $R_1$ is phenyl, naphthyl or thienyl optionally substituted by $C_{6-10}$aryl$C_{0-4}$alkyl, $C_{2-9}$heteroaryl$C_{0-4}$alkyl, $C_{3-8}$cycloalkyl$C_{0-4}$alkyl, $C_{3-8}$heterocycloalkyl$C_{0-4}$alkyl or $C_{1-6}$alkyl; wherein any aryl, heteroaryl, cycloalkyl or heterocycloalkyl group of $R_1$ can be optionally substituted by one to five radicals chosen from halo, $C_{1-6}$alkyl, $C_{1-6}$alkoxy, halo-substituted-$C_{1-6}$alkyl and halo-substituted-$C_{1-6}$alkoxy; and any alkyl group of $R_1$ can optionally have a methylene replaced by an atom or group chosen from —S—, —S(O), —S(O)$_2$—, —NR$_5$— and —O—; wherein $R_5$ is hydrogen or $C_{1-6}$alkyl.

In another embodiment, Y is chosen from:

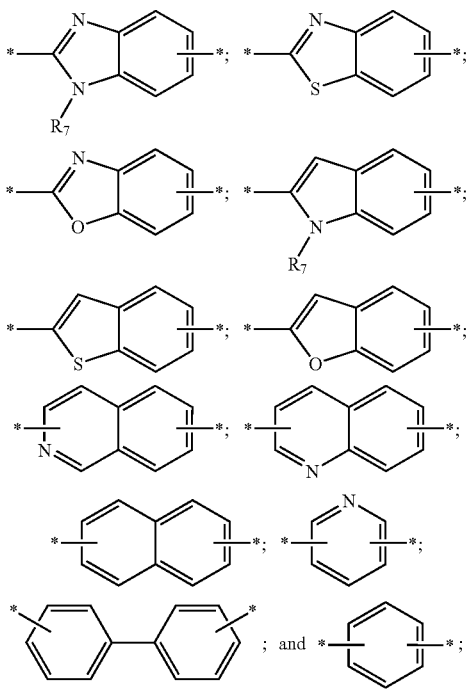

wherein $R_7$ is hydrogen or $C_{1-6}$alkyl; and the left and right asterisks of Y indicate the point of attachment a) either between —C(R$_2$)═NOWR$_1$ and the —CR$_3$R$_4$—, or between —CR$_3$R$_4$— and —C(R$_2$)═NOWR$_1$ of Formula Ia, respectively, or b) either between —CR$_3$R$_4$— and W or between W and —CR$_3$R$_4$— of Formula Ib, respectively; wherein any aryl or heteroaryl of Y can be optionally substituted with 1 to 3 radicals chosen from halo, hydroxy, nitro, $C_{1-6}$alkyl, $C_{1-6}$alkoxy, halo-substituted $C_{1-6}$alkyl and halo-substituted $C_{1-6}$alkoxy.

In a further embodiment, $R_1$ is chosen from:

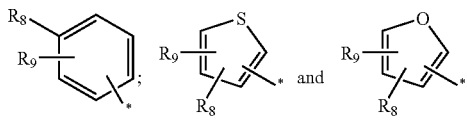

wherein the asterisk is the point of attachment of $R_1$ with W; $R_8$ is $C_{6-10}$aryl$C_{0-4}$alkyl, $C_{2-9}$heteroaryl$C_{0-4}$alkyl, $C_{3-8}$cycloalkyl$C_{0-4}$alkyl, $C_{3-8}$heterocycloalkyl$C_{0-4}$alkyl or $C_{1-6}$alkyl; wherein any aryl, heteroaryl, cycloalkyl or heterocycloalkyl group of $R_8$ can be optionally substituted by one to three radicals chosen from halo, $C_{1-6}$alkyl, $C_{1-6}$alkoxy, halo-substituted-$C_{1-6}$alkyl and halo-substituted-$C_{1-6}$alkoxy; and any alkyl group of $R_9$ can optionally have a methylene replaced by an atom or group chosen from —S—, —S(O), —S(O)$_2$—, —NR$_5$— and —O—; wherein $R_5$ is hydrogen or $C_{1-6}$alkyl; and $R_9$ is chosen from halo, $C_{1-6}$alkyl, $C_{1-6}$alkoxy, halo-substituted-$C_{1-6}$alkyl and halo-substituted-$C_{1-6}$alkoxy.

In another embodiment, A is —C(O)OH; Z is chosen from:

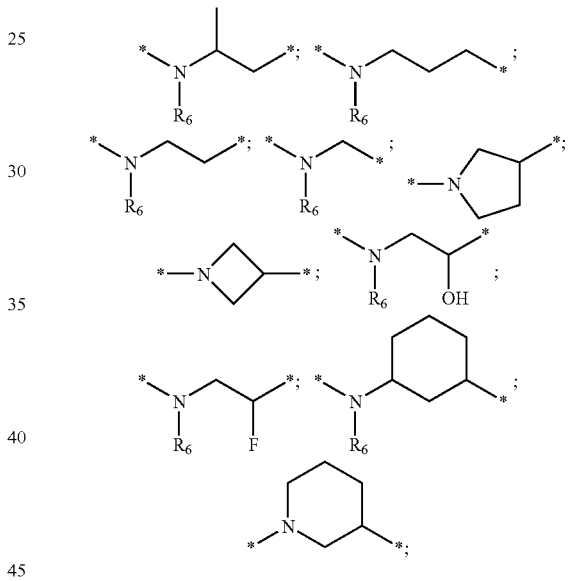

wherein the left and right asterisks of Z indicate the point of attachment between —C(R$_3$)(R$_4$)— and A of Formula Ia or Ib, respectively; $R_6$ is chosen from hydrogen and $C_{1-6}$alkyl; and $R_3$ and $R_4$ are both hydrogen.

In a further embodiment, Y is chosen from phenyl, pyridinyl, thienyl and furanyl; wherein any phenyl, pyridinyl, thienyl or furanyl of Y is optionally substituted with 1 to 3 radicals chosen from methyl, ethyl, cyclopropyl, chloro, bromo, fluoro and methoxy; or where Y is phenyl, $R_6$ can be attached to a carbon atom of Y to form 3,4-dihydro-1H-isoquinolin-2-yl.

In another embodiment, W is a bond or methylene; $R_1$ is chosen from:

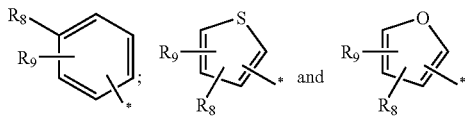

wherein $R_8$ is chosen from phenyl, cyclohexyl, thienyl, 3,3-dimethyl-butyl, pyridinyl, cyclopentyl and piperidinyl; wherein $R_8$ can be optionally substituted by 1 to 3 radicals chosen from trifluoromethyl, methoxy, fluoro, trifluoromethoxy and methyl; and $R_9$ is chosen from trifluoromethyl, fluoro, methyl, chloro, methoxy and ethyl.

Preferred compounds of the invention include: 3-{4-[1-(2-Trifluoromethyl-biphenyl-4-ylmethoxyimino)-ethyl]-benzylamino}-propionic acid, 3-{4-[1-(4-Cyclohexyl-3-trifluoromethyl-benzyloxyimino)-ethyl]-2-ethyl-benzylamino}-propionic acid, 1-{4-[1-(4-Cyclohexyl-3-trifluoromethyl-benzyloxyimino)-ethyl]-2-ethyl-benzyl}-azetidine-3-carboxylic acid, 3-({2-Chloro-6-[1-(4-cyclohexyl-3-trifluoromethyl-benzyloxyimino)-ethyl]-pyridin-3-ylmethyl}-amino)-propionic acid, 3-({6-[1-(4-Cyclohexyl-3-trifluoromethyl-benzyloxyimino)-ethyl]-2-ethyl-pyridin-3-ylmethyl}-amino)-propionic acid, 3-{4-[1-(Biphenyl-4-ylmethoxyimino)-ethyl]-benzylamino}-propionic acid, 4-{4-[1-(Biphenyl-4-ylmethoxyimino)-ethyl]-benzylamino}-butyric acid, 1-{4-[1-(Biphenyl-4-ylmethoxyimino)-ethyl]-benzyl}-azetidine-3-carboxylic acid, 1-{4-[1-(Biphenyl-4-ylmethoxyimino)-ethyl]-benzyl}-piperidine-3-carboxylic acid, {4-[1-(Biphenyl-4-ylmethoxyimino)-ethyl]-benzylamino}-acetic acid, 3-{4-[1-(Biphenyl-4-ylmethoxyimino)-ethyl]-benzylamino}-cyclopentanecarboxylic acid, 3-{4-[1-(4'-Trifluoromethyl-biphenyl-4-ylmethoxyimino)-ethyl]-benzylamino}-propionic acid, 3-{4-[1-(5-Phenyl-furan-2-ylmethoxyimino)-ethyl]-benzylamino}-propionic acid, 3-{4-[1-(3'-Trifluoromethyl-biphenyl-4-ylmethoxyimino)-ethyl]-benzylamino}-propionic acid, 3-{4-[1-(3-Trifluoromethyl-biphenyl-4-ylmethoxyimino)-ethyl]-benzylamino}-propionic acid, 3-{4-[1-(4'-Methoxy-biphenyl-4-ylmethoxyimino)-ethyl]-benzylamino}-propionic acid, 3-{4-[1-(Biphenyl-3-ylmethoxyimino)-ethyl]-benzylamino}-propionic acid, 3-{4-[1-(4-Thiophen-2-yl-benzyloxyimino)-ethyl]-benzylamino}-propionic acid, 3-{4-[1-(4-Thiophen-2-yl-3-trifluoromethyl-benzyloxyimino)-ethyl]-benzylamino}-propionic acid, 3-{4-[1-(4'-Fluoro-biphenyl-4-ylmethoxyimino)-ethyl]-benzylamino}-propionic acid, 3-{4-[1-(4'-Trifluoromethoxy-biphenyl-4-ylmethoxyimino)-ethyl]-benzylamino}-propionic acid, 3-{4-[1-(3'-Trifluoromethoxy-biphenyl-4-ylmethoxyimino)-ethyl]-benzylamino}-propionic acid, 1-{4-[1-(2-Trifluoromethyl-biphenyl-4-ylmethoxyimino)-ethyl]-benzyl}-azetidine-3-carboxylic acid, 1-{4-[1-(2-Trifluoromethyl-biphenyl-4-ylmethoxyimino)-ethyl]-benzyl}-pyrrolidine-3-carboxylic acid, 1-{4-[1-(2-Trifluoromethyl-biphenyl-4-ylmethoxyimino)-ethyl]-benzyl}-piperidine-3-carboxylic acid, 3-{4-[1-(3'-Methoxy-biphenyl-4-ylmethoxyimino)-ethyl]-benzylamino}-propionic acid, 2-Hydroxy-3-{4-[1-(2-trifluoromethyl-biphenyl-4-ylmethoxyimino)-ethyl]-benzylamino}-propionic acid, 3-{4-[1-(4'-Methyl-biphenyl-4-ylmethoxyimino)-ethyl]-benzylamino}-propionic acid, 3-{4-[1-(4-Phenyl-thiophen-2-ylmethoxyimino)-ethyl]-benzylamino}-propionic acid, 1-{4-[1-(Biphenyl-4-ylmethoxyimino)-ethyl]-benzyl}-pyrrolidine-3-carboxylic acid, 3-{4-[1-(4-Furan-3-yl-benzyloxyimino)-ethyl]-benzylamino}-propionic acid, 3-{4-[1-(4-Thiophen-3-yl-3-trifluoromethyl-benzyloxyimino)-ethyl]-benzylamino}-propionic acid, 3-{4-[1-(4-Thiophen-3-yl-2-trifluoromethyl-benzyloxyimino)-ethyl]-benzylamino}-propionic acid, 2-Fluoro-3-{4-[1-(2-trifluoromethyl-biphenyl-4-ylmethoxyimino)-ethyl]-benzylamino}-propionic acid, 3-{4-[1-(2-Trifluoromethyl-biphenyl-4-ylmethoxyimino)-ethyl]-benzylamino}-butyric acid, 3-{4-[1-(5-Phenyl-thiophen-2-ylmethoxyimino)-ethyl]-benzylamino}-propionic acid, 3-{4-[1-(4-Cyclohexyl-benzyloxyimino)-ethyl]-benzylamino}-propionic acid, 3-{4-[1-(3-Fluoro-biphenyl-4-ylmethoxyimino)-ethyl]-benzylamino}-propionic acid, 3-{4-[1-(4'-Fluoro-2-trifluoromethyl-biphenyl-4-ylmethoxyimino)-ethyl]-benzylamino}-propionic acid, 3-{4-[1-(4'-Methyl-2-trifluoromethyl-biphenyl-4-ylmethoxyimino)-ethyl]-benzylamino}-propionic acid, 3-{4-[1-(4-Furan-2-yl-3-trifluoromethyl-benzyloxyimino)-ethyl]-benzylamino}-propionic acid, 3-{4-[1-(2'-Fluoro-2-trifluoromethyl-biphenyl-4-ylmethoxyimino)-ethyl]-benzylamino}-propionic acid, 3-(4-{1-[4-(3,3-Dimethyl-butyl)-3-trifluoromethyl-benzyloxyimino]-ethyl}-benzylamino)-propionic acid, 3-{4-[1-(4-Furan-3-yl-3-trifluoromethyl-benzyloxyimino)-ethyl]-benzylamino}-propionic acid, 3-{4-[1-(4-Pyridin-3-yl-benzyloxyimino)-ethyl]-benzylamino}-propionic acid, 3-{4-[1-(4-Pyridin-4-yl-benzyloxyimino)-ethyl]-benzylamino}-propionic acid, 3-{4-[1-(2-Fluoro-biphenyl-4-ylmethoxyimino)-ethyl]-benzylamino}-propionic acid, 3-({2-Methoxy-6-[1-(2-trifluoromethyl-biphenyl-4-ylmethoxyimino)-ethyl]-pyridin-3-ylmethyl}-amino)-propionic acid, 3-{4-[1-(4-Cyclohexyl-3-trifluoromethyl-benzyloxyimino)-ethyl]-2-ethyl-benzylamino}-propionic acid, 3-{4-[1-(4-Cyclohexyl-3-trifluoromethyl-benzyloxyimino)-ethyl]-benzylamino}-propionic acid, 3-{2-Bromo-4-[1-(4-cyclohexyl-3-trifluoromethyl-benzyloxyimino)-ethyl]-benzylamino}-propionic acid, 3-{4-[1-(4-Cyclopentyl-3-trifluoromethyl-benzyloxyimino)-ethyl]-benzylamino}-propionic acid, 3-{2-Chloro-4-[1-(4-cyclohexyl-3-trifluoromethyl-benzyloxyimino)-ethyl]-benzylamino}-propionic acid, 3-({6-[1-(4-Cyclohexyl-3-trifluoromethyl-benzyloxyimino)-ethyl]-pyridin-3-ylmethyl}-amino)-propionic acid, 3-({5-[1-(4-Cyclohexyl-3-trifluoromethyl-benzyloxyimino)-ethyl]-thiophen-2-ylmethyl}-amino)-propionic acid, 3-({5-[1-(4-Cyclohexyl-3-trifluoromethyl-benzyloxyimino)-ethyl]-pyridin-2-ylmethyl}-amino)-propionic acid, 3-({5-[1-(4-Cyclohexyl-3-trifluoromethyl-benzyloxyimino)-ethyl]-furan-2-ylmethyl}-amino)-propionic acid, 3-({2-[1-(4-Cyclohexyl-3-trifluoromethyl-benzyloxyimino)-ethyl]-pyridin-4-ylmethyl}-amino)-propionic acid, 3-{4-[1-(4-Cyclohexyl-3-fluoro-benzyloxyimino)-ethyl]-benzylamino}-propionic acid, 3-{2-Chloro-4-[1-(4-cyclohexyl-3-trifluoromethyl-benzyloxyimino)-ethyl]-benzylamino}-propionic acid, 1-{6-[1-(4-Cyclohexyl-3-trifluoromethyl-benzyloxyimino)-ethyl]-2-ethyl-pyridin-3-ylmethyl}-azetidine-3-carboxylic acid, 3-{2-Ethyl-4-[1-(4-piperidin-1-yl-3-trifluoromethyl-benzyloxyimino)-ethyl]-benzylamino}-propionic acid, 3-{4-[1-(4-Cyclohexyl-3-methyl-benzyloxyimino)-ethyl]-2-ethyl-benzylamino}-propionic acid, 3-{4-[1-(3-Chloro-4-cyclohexyl-benzyloxyimino)-ethyl]-2-ethyl-benzylamino}-propionic acid, 3-{4-[1-(4-Cyclohexyl-3-methoxy-benzyloxyimino)-ethyl]-2-ethyl-benzylamino}-propionic acid, 1-{4-[1-(4-Cyclohexyl-3-methoxy-benzyloxyimino)-ethyl]-2-ethyl-benzyl}-azetidine-3-carboxylic acid, 3-{4-[1-(4-Cyclohexyl-3-trifluoromethyl-benzyloxyimino)-ethyl]-2-methyl-benzylamino}-propionic acid, 1-{4-[1-(4-Cyclohexyl-3-trifluoromethyl-benzyloxyimino)-ethyl]-2-methyl-benzyl}-azetidine-3-carboxylic acid, 3-{4-[1-(4-Cyclohexyl-3-trifluoromethyl-benzyloxyimino)-ethyl]-2-cyclopropyl-benzylamino}-propionic acid, 1-{4-[1-(4-Cyclohexyl-3-trifluoromethyl-benzyloxyimino)-ethyl]-2-cyclopropyl-benzyl}-azetidine-3-carboxylic acid, 3-{2-Ethyl-4-[1-(2-trifluoromethyl-biphenyl-4-ylmethoxyimino)-ethyl]-benzylamino}-propionic acid, 1-{4-[1-(4-Cyclohexyl-3-ethyl-benzyloxyimino)-ethyl]-2-ethyl-benzyl}-azetidine-3-carboxylic acid, 1-{4-[1-(4-Cyclohexyl-3-methylbenzyloxyimino)-ethyl]-2-ethyl-benzyl}-azetidine-3-carboxylic acid, 1-{2-Chloro-4-[1-(4-cyclohexyl-3-ethyl-benzyloxyimino)-ethyl]-benzyl}-azetidine-3-carboxylic acid, 3-{2-Chloro-4-[1-(4-cyclohexyl-3-ethyl-benzyloxyimino)-ethyl]-benzylamino}-propionic acid, 3-{4-[1-(4-Cyclohexyl-3-trifluoromethyl-benzyloxyimino)-ethyl]-2-fluoro-benzylamino}-propionic acid, 1-{4-[1-(4-Cyclohexyl-3-trifluoromethyl-benzyloxyimino)-ethyl]-2-fluoro-benzyl}-azetidine-3-carboxylic acid, 3-{6-[1-(4-Cyclohexyl-3-trifluoromethyl-benzyloxyimino)-ethyl]-3,4-dihydro-1H-isoquinolin-2-yl}-propionic acid, 3-{6-[1-(4-Cyclohexyl-3-ethyl-benzyloxyimino)-ethyl]-3,4-dihydro-1H-isoquinolin-2-yl}-propionic acid, 3-{4-[1-(2-Trifluoromethyl-biphenyl-4-yl)-ethylideneaminooxymethyl]-benzylamino}-propionic acid, 3-{4-[1-(4-Cyclohexyl-3-trifluoromethyl-phenyl)-ethylideneaminooxymethyl]-benzylamino}-propionic acid, 3-{4-[1-(4-Cyclohexyl-3-trifluoromethyl-phenyl)-ethylideneaminooxymethyl]-2-ethyl-benzylamino}-propionic acid, 1-{4-[1-(4-Cyclohexyl-3-trifluoromethyl-phenyl)-ethylideneaminooxymethyl]-2-ethyl-benzyl}-azetidine-3-carboxylic acid and 1-{4-[1-(4-Cyclohexyl-3-ethyl-phenyl)-ethylideneaminooxymethyl]-2-ethyl-benzyl}-azetidine-3-carboxylic acid. Further, preferred compounds are also shown in the examples and table 1, infra.

The invention provides forms of the compound that have the hydroxyl or amine group present in a protected form; these function as prodrugs. Prodrugs are compounds that are converted into an active drug form after administration, through one or more chemical or biochemical transformations. Forms of the compounds of the present invention that are readily converted into the claimed compound under physiological conditions are prodrugs of the claimed compounds and are within the scope of the present invention. Examples of prodrugs include forms where a hydroxyl group is acylated to form a relatively labile ester such as an acetate ester, and forms where an amine group is acylated with the carboxylate group of glycine or an L-amino acid such as serine, forming an amide bond that is particularly susceptible to hydrolysis by common metabolic enzymes.

Compounds of Formula Ia or Ib can exist in free form or in salt form, e.g. addition salts with inorganic or organic acids. Where hydroxyl groups are present, these groups can also be present in salt form, e.g. an ammonium salt or salts with metals such as lithium, sodium, potassium, calcium, zinc or magnesium, or a mixture thereof. Compounds of Formula Ia or Ib and their salts in hydrate or solvate form are also part of the invention.

When the compounds of Formula Ia or Ib have asymmetric centers in the molecule, various optical isomers are obtained. The present invention also encompasses enantiomers, racemates, diastereoisomers and mixtures thereof. Moreover, when the compounds of Formula Ia or Ib include geometric isomers, the present invention embraces cis-compounds, trans-compounds and mixtures thereof. Similar considerations apply in relation to starting materials exhibiting asymmetric carbon atoms or unsaturated bonds as mentioned above.

Methods and Pharmaceutical Compositions for Treating Immunomodulatory Conditions The compounds of Formula Ia or Ib in free form or in pharmaceutically acceptable salt form, exhibit valuable pharmacological properties, e.g. lymphocyte recirculation modulating properties, for example, as indicated by the in vitro and in vivo tests of Example 6 and are therefore indicated for therapy. Compounds of Formula Ia or Ib preferably show an $EC_{50}$ in the range of $1\times10^{-11}$ to $1\times10^{-5}$ M, preferably less than 50 nM. The compounds exhibit selectivity for one or more EDG/S1P receptors, preferably EDG-1/S1P-1. EDG-1/S1P-1 selective modulators of the present invention can be identified by assaying a compound's binding to EDG-1/S1P-1 and one or more of the other EDG/S1P receptors (e.g., EDG-3/S1P-3, EDG-5/S1P-2, EDG-6/S1P-4, and EDG-8/S1P-5). An EDG-1/S1P-1 selective modulator usually has an EC50 for the EDG-1/S1P-1 receptor in the range of $1\times10^{-1}$ to $1\times10^{-5}$ M, preferably less than 50 nM, more preferably less than 5 nM. It also has an EC50 for one or more of the other EDG/S1P receptors that is at least 5, 10, 25, 50, 100, 500, or 1000 fold higher than its EC50 for EDG-1/S1P-1. Thus, some of the EDG-1/S1P-1 modulatory compounds will have an EC50 for EDG-1/S1P-1 that is less than 5 nM while their EC50 for one or more of the other EDG/S1P receptors are at least 100 nM or higher. Other than assaying binding activity to the EDG/S1P receptors, EDG-1/S1P-1 selective agents can also be identified by examining a test agent's ability to modify a cellular process or activity mediated by an EDG/S1P receptor.

The compounds of Formula Ia or Ib are, therefore, useful in the treatment and/or prevention of diseases or disorders mediated by lymphocytes interactions, for example in transplantation, such as acute or chronic rejection of cell, tissue or organ allo- or xenografts or delayed graft function, graft versus host disease, autoimmune diseases, e.g. rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, psoriasis, Graves ophthalmopathy, alopecia areata and others, allergic diseases, e.g. allergic asthma, atopic dermatitis, allergic rhinitis/conjunctivitis, allergic contact dermatitis, inflammatory diseases optionally with underlying aberrant reactions, e.g. inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, myocarditis or hepatitis, ischemia/reperfusion injury, e.g. myocardial infarction, stroke, gut ischemia, renal failure or hemorrhage shock, traumatic shock, T cell lymphomas or T cell leukemias, infectious diseases, e.g. toxic shock (e.g. superantigen induced), septic shock, adult respiratory distress syndrome or viral infections, e.g. AIDS, viral hepatitis, chronic bacterial infection, or senile dementia. Examples of cell, tissue or solid organ transplants include e.g. pancreatic islets, stem cells, bone marrow, corneal tissue, neuronal tissue, heart, lung, combined heart-lung, kidney, liver, bowel, pancreas, trachea or oesophagus. For the above uses the required dosage will of course vary depending on the mode of administration, the particular condition to be treated and the effect desired.

Furthermore, the compounds of Formula Ia or Ib are useful in cancer chemotherapy, particularly for cancer chemotherapy of solid tumors, e.g. breast cancer, or as an anti-angiogenic agent.

The required dosage will of course vary depending on the mode of administration, the particular condition to be treated and the effect desired. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, for example, in divided doses up to four times a day or in retard form. Suitable unit dosage forms for oral administration comprise from ca. 1 to 50 mg active ingredient.

The compounds of Formula Ia or Ib can be administered by any conventional route, in particular enterally, for example, orally, e.g. in the form of tablets or capsules, or parenterally, for example, in the form of injectable solutions or suspensions, topically, e.g. in the form of lotions, gels, ointments or creams, or in a nasal or a suppository form. Pharmaceutical compositions comprising a compound of Formula Ia or Ib in free form or in pharmaceutically acceptable salt form in association with at least one pharmaceutical acceptable carrier or diluent can be manufactured in conventional manner by mixing with a pharmaceutically acceptable carrier or diluent.

The compounds of Formula Ia or Ib can be administered in free form or in pharmaceutically acceptable salt form, for example, as indicated above. Such salts can be prepared in a conventional manner and exhibit the same order of activity as the free compounds.

In accordance with the foregoing the present invention further provides:

1.1 A method for preventing or treating disorders or diseases mediated by lymphocytes, e.g. such as indicated above, in a subject in need of such treatment, which method comprises administering to said subject an effective amount of a compound of Formula Ia or Ib or a pharmaceutically acceptable salt thereof;

1.2 A method for preventing or treating acute or chronic transplant rejection or T-cell mediated inflammatory or autoimmune diseases, e.g. as indicated above, in a subject in need of such treatment, which method comprises administering to said subject an effective amount of a compound of Formula Ia or Ib or a pharmaceutically acceptable salt thereof;

1.3 A method for inhibiting or controlling deregulated angiogenesis, e.g. sphingosine-1-phosphate (S1P) mediated angiogenesis, in a subject in need thereof, comprising administering to said subject a therapeutically effective amount of a compound of Formula Ia or Ib or a pharmaceutically acceptable salt thereof.

1.4 A method for preventing or treating diseases mediated by a neo-angiogenesis process or associated with deregulated angiogenesis in a subject in need thereof, comprising administering to said subject a therapeutically effective amount of a compound of Formula Ia or Ib or a pharmaceutically acceptable salt thereof.

2. A compound of Formula Ia or Ib, in free form or in a pharmaceutically acceptable salt form for use as a pharmaceutical, e.g. in any of the methods as indicated under 1.1 to 1.4 above.

3. A pharmaceutical composition, e.g. for use in any of the methods as in 1.1 to 1.4 above comprising a compound of Formula Ia or Ib in free form or pharmaceutically acceptable salt form in association with a pharmaceutically acceptable diluent or carrier therefor.

4. A compound of Formula Ia or Ib or a pharmaceutically acceptable salt thereof for use in the preparation of a pharmaceutical composition for use in any of the method as in 1.1 to 1.4 above.

The compounds of Formula Ia or Ib may be administered as the sole active ingredient or in conjunction with, e.g. as an adjuvant to, other drugs e.g. immunosuppressive or immunomodulating agents or other anti-inflammatory agents, e.g. for the treatment or prevention of allo- or xenograft acute or chronic rejection or inflammatory or autoimmune disorders, or a chemotherapeutic agent, e.g. a malignant cell anti-proliferative agent. For example the compounds of Formula Ia or Ib may be used in combination with a calcineurin inhibitor, e.g. cyclosporin A or FK 506; a mTOR inhibitor, e.g. rapamycin, 40-O-(2-hydroxyethyl)-rapamycin, CCI779, ABT578 or AP23573; an ascomycin having immunosuppressive properties, e.g. ABT-281, ASM981, etc.; corticosteroids; cyclophosphamide; azathioprene; methotrexate; leflunomide; mizoribine; mycophenolic acid; mycophenolate mofetil; 15-deoxyspergualine or an immunosuppressive homologue, analogue or derivative thereof; immunosuppressive monoclonal antibodies, e.g. monoclonal antibodies to leukocyte receptors, e.g. MHC, CD2, CD3, CD4, CD7, CD8, CD25, CD28, CD40. CD45, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or a chemotherapeutic agent.

By the term "chemotherapeutic agent" is meant any chemotherapeutic agent and it includes but is not limited to, i. an aromatase inhibitor, ii. an anti-estrogen, an anti-androgen (especially in the case of prostate cancer) or a gonadorelin agonist, iii. a topoisomerase I inhibitor or a topoisomerase II inhibitor, iv. a microtubule active agent, an alkylating agent, an antineoplastic antimetabolite or a platin compound, v. a compound targeting/decreasing a protein or lipid kinase activity or a protein or lipid phosphatase activity, a further anti-angiogenic compound or a compound which induces cell differentiation processes, vi. a bradykinin 1 receptor or an angiotensin II antagonist, vii. a cyclooxygenase inhibitor, a bisphosphonate, a histone deacetylase inhibitor, a heparanase inhibitor (prevents heparan sulphate degradation), e.g. PI-88, a biological response modifier, preferably a lymphokine or interferons, e.g. interferon □, an ubiquitination inhibitor, or an inhibitor which blocks anti-apoptotic pathways, viii. an inhibitor of Ras oncogenic isoforms, e.g. H-Ras, K-Ras or N-Ras, or a farnesyl transferase inhibitor, e.g. L-744,832 or DK8G557, ix. a telomerase inhibitor, e.g. telomestatin, x. a protease inhibitor, a matrix metalloproteinase inhibitor, a methionine aminopeptidase inhibitor, e.g. bengamide or a derivative thereof, or a proteosome inhibitor, e.g. PS-341, and/or xi. a mTOR inhibitor.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketoconazole, vorozole, fadrozole, anastrozole and letrozole. A combination of the invention comprising a chemotherapeutic agent which is an aromatase inhibitor is particularly useful for the treatment of hormone receptor positive tumors, e.g. breast tumors.

The term "anti-estrogen" as used herein relates to a compound which antagonizes the effect of estrogens at the estrogen receptor level. The term includes, but is not limited to tamoxifen, fulvestrant, raloxifene and raloxifene hydrochloride. A combination of the invention comprising a chemotherapeutic agent which is an anti-estrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide.

The term "gonadorelin agonist" as used herein includes, but is not limited to abarelix, goserelin and goserelin acetate.

The term "topoisomerase I inhibitor" as used herein includes, but is not limited to topotecan, irinotecan, 9-nitro-camptothecin and the macromolecular camptothecin conjugate PNU-166148 (compound A1 in WO99/17804).

The term "topoisomerase II inhibitor" as used herein includes, but is not limited to the anthracyclines such as doxorubicin, daunorubicin, epirubicin, idarubicin and nemorubicin, the anthraquinones mitoxantrone and losoxantrone, and the podophillotoxines etoposide and teniposide.

The term "microtubule active agent" relates to microtubule stabilizing and microtubule destabilizing agents including, but not limited to taxanes, e.g. paclitaxel and docetaxel, vinca alkaloids, e.g., vinblastine, especially vinblastine sulfate, vincristine especially vincristine sulfate, and vinorelbine, discodermolides and epothilones and derivatives thereof, e.g. epothilone B or a derivative thereof.

The term "alkylating agent" as used herein includes, but is not limited to busulfan, chlorambucil, cyclophosphamide, ifosfamide, melphalan or nitrosourea (BCNU or Gliadel™).

The term "antineoplastic antimetabolite" includes, but is not limited to 5-fluorouracil, capecitabine, gemcitabine, cytarabine, fludarabine, thioguanine, methotrexate and edatrexate.

The term "platin compound" as used herein includes, but is not limited to carboplatin, cis-platin and oxaliplatin.

The term "compounds targeting/decreasing a protein or lipid kinase activity or further anti-angiogenic compounds" as used herein includes, but is not limited to protein tyrosine kinase and/or serine and/or threonine kinase inhibitors or lipid kinase inhibitors, e.g. compounds targeting, decreasing or inhibiting the activity of the epidermal growth factor family of receptor tyrosine kinases (EGFR, ErbB2, ErbB3, ErbB4 as homo- or heterodimers), the vascular endothelial growth factor family of receptor tyrosine kinases (VEGFR), the platelet-derived growth factor-receptors (PDGFR), the fibroblast growth factor-receptors (FGFR), the insulin-like growth factor receptor 1 (IGF-1R), the Trk receptor tyrosine kinase family, the Ax1 receptor tyrosine kinase family, the Ret receptor tyrosine kinase, the Kit/SCFR receptor tyrosine kinase, members of the c-Abl family and their gene-fusion products (e.g. BCR-Abl), members of the protein kinase C (PKC) and Raf family of serine/threonine kinases, members of the MEK, SRC, JAK, FAK, PDK or PI(3) kinase family, or of the PI(3)-kinase-related kinase family, and/or members of the cyclin-dependent kinase family (CDK) and anti-angiogenic compounds having another mechanism for their activity, e.g. unrelated to protein or lipid kinase inhibition.

Compounds which target, decrease or inhibit the activity of VEGFR are especially compounds, proteins or antibodies which inhibit the VEGF receptor tyrosine kinase, inhibit a VEGF receptor or bind to VEGF, and are in particular those compounds, proteins or monoclonal antibodies generically and specifically disclosed in WO 98/35958, e.g. 1-(4-chloroanilino)-4-(4-pyridylmethyl)phthalazine or a pharmaceutically acceptable salt thereof, e.g. the succinate, in WO 00/27820, e.g. a N-aryl(thio) anthranilic acid amide derivative e.g. 2-[(4-pyridyl)methyl]amino-N-[3-methoxy-5-(trifluoromethyl)phenyl]benzamide or 2-[(1-oxido-4-pyridyl)methyl]amino-N-[3-trifluoromethylphenyl]benzamide, or in WO 00/09495, WO 00/59509, WO 98/11223, WO 00/27819 and EP 0 769 947; those as described by M. Prewett et al in Cancer Research 59 (1999) 5209-5218, by F. Yuan et al in Proc. Natl. Acad. Sci. USA, vol. 93, pp. 14765-14770, December 1996, by Z. Zhu et al in Cancer Res. 58, 1998, 3209-3214, and by J. Mordenti et al in Toxicologic Pathology, Vol. 27, no. 1, pp 14-21, 1999; in WO 00/37502 and WO 94/10202; Angiostatin™, described by M. S. O'Reilly et al, Cell 79, 1994, 315-328; Endostatin™, described by M. S. O'Reilly et al, Cell 88, 1997, 277-285; anthranilic acid amides; ZD4190; ZD6474; SU5416; SU6668; or anti-VEGF antibodies or anti-VEGF receptor antibodies, e.g. RhuMab.

By antibody is meant intact monoclonal antibodies, polyclonal antibodies, multispecific antibodies formed from at least 2 intact antibodies, and antibody fragments so long as they exhibit the desired biological activity.

Compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, or which have a dual inhibiting effect on the ErbB and VEGF receptor kinase and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180) or PCT/EP02/08780; e.g. trastuzumab (HerpetinR), cetuximab, Iressa, OSI-774, CI-1033, EKB-569, GW-2016, E1.1, E2.4, E2.5, E6.2, E6.4, E2.11, E6.3 or E7.6.3.

Compounds which target, decrease or inhibit the activity of PDGFR are especially compounds which inhibit the PDGF receptor, e.g. a N-phenyl-2-pyrimidine-amine derivative, e.g. imatinib.

Compounds which target, decrease or inhibit the activity of c-Abl family members and their gene fusion products are, e.g. a N-phenyl-2-pyrimidine-amine derivative, e.g. imatinib; PD180970; AG957; or NSC 680410.

Compounds which target, decrease or inhibit the activity of protein kinase C, Raf, MEK, SRC, JAK, FAK and PDK family members, or PI(3) kinase or PI(3) kinase-related family members, and/or members of the cyclin-dependent kinase family (CDK) are especially those staurosporine derivatives disclosed in EP 0 296 110, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; or LY333531/LY379196.

Further anti-angiogenic compounds are e.g. thalidomide (THALOMID) and TNP-470.

Compounds which target, decrease or inhibit the activity of a protein or lipid phosphatase are, e.g. inhibitors of phosphatase 1, phosphatase 2A, PTEN or CDC25, e.g. okadaic acid or a derivative thereof.

Compounds which induce cell differentiation processes are, e.g. retinoic acid, α-, γ- or δ-tocopherol or α-, γ- or δ-tocotrienol.

The term cyclooxygenase inhibitor as used herein includes, but is not limited to, e.g. celecoxib (Celebrex®), rofecoxib (Vioxx®), etoricoxib, valdecoxib or a 5-alkyl-2-arylaminophenylacetic acid, e.g. 5-methyl-2-(2'-chloro-6'-fluoroanilino)phenyl acetic acid.

The term "histone deacetylase inhibitor" as used herein includes, but is not limited to MS-27-275, SAHA, pyroxamide, FR-901228 or valproic acid.

The term "bisphosphonates" as used herein includes, but is not limited to, etridonic, clodronic, tiludronic, pamidronic, alendronic, ibandronic, risedronic and zoledronic acid.

The term "matrix metalloproteinase inhibitor" as used herein includes, but is not limited to collagen peptidomimetic and non-petidomimetic inhibitors, tetracycline derivatives, e.g. hydroxamate peptidomimetic inhibitor batimastat and its orally bioavailable analogue marimastat, prinomastat, BMS-279251, BAY 12-9566, TAA211 or AAJ996.

The term "mTOR inhibitor" as used herein includes, but is not limited to rapamycin (sirolimus) or a derivative thereof, e.g. 32-deoxorapamycin, 16-pent-2-ynyloxy-32-deoxorapamycin, 16-pent-2-ynyloxy-32(S)-dihydro-rapamycin, 16-pent-2-ynyloxy-32(S)-dihydro-40-O-(2-hydroxyethyl)-rapamycin and, more preferably, 40-O-(2-hydroxy-ethyl)-rapamycin. Further examples of rapamycin derivatives include e.g. CCI779 or 40-[3-hydroxy-2-(hydroxymethyl)-2-methyl-propanoate]-rapamycin or a pharmaceutically acceptable salt thereof, as disclosed in U.S. Pat. No. 5,362,718, ABT578 or 40-(tetrazolyl)-rapamycin, particularly 40-epi-(tetrazolyl)-rapamycin, e.g. as disclosed in WO 99/15530, or rapalogs as disclosed e.g. in WO 98/02441 and WO01/14387, e.g. AP23573.

Where the compounds of Formula Ia or Ib are administered in conjunction with other immunosuppressive/immunomodulatory, anti-inflammatory or chemotherapeutic therapy, dosages of the co-administered immunosuppressant, immunomodulatory, anti-inflammatory or chemotherapeutic compound will of course vary depending on the type of co-drug employed, e.g. whether it is a steroid or a calcineurin inhibitor, on the specific drug employed, on the condition being treated and so forth.

In accordance with the foregoing the present invention provides in a yet further aspect:

5. A method as defined above comprising co-administration, e.g. concomitantly or in sequence, of a therapeutically effective non-toxic amount of a compound of Formula Ia or Ib and at least a second drug substance, e.g. an immunosuppressant, immunomodulatory, anti-inflammatory or chemotherapeutic drug, e.g. as indicated above.

6. A pharmaceutical combination, e.g. a kit, comprising a) a first agent which is a compound of Formula Ia or Ib as disclosed herein, in free form or in pharmaceutically acceptable salt form, and b) at least one co-agent, e.g. an immunosuppressant, immunomodulatory, anti-inflammatory or chemotherapeutic drug, e.g. as disclosed above. The kit may comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula Ia or Ib and a co-agent, are both administered to a patient simultaneously in the form of a single entity or dosage. The term "non-fixed combination" means that the active ingredients, e.g. a compound of Formula Ia or Ib and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Methods for Preparing Compounds of the Invention

The present invention also includes processes for the preparation of immunomodulatory compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula Ia, in which A is $R_5OC(O)$— and $R_3$ and $R_4$ are hydrogen, can be prepared by proceeding as in the following reaction scheme:

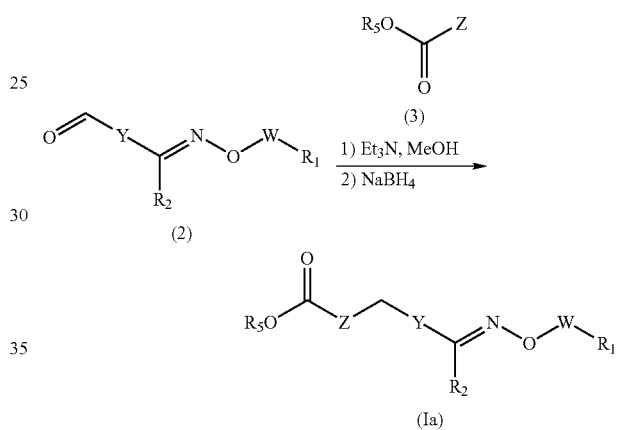

in which W, Y, Z, $R_1$, $R_2$, and $R_5$ are as defined for Formula Ia above. Compounds of Formula I can be prepared by reacting a compound of formula 2 with a compound of formula 3 in the presence of a suitable solvent (e.g. methanol, and the like), a suitable base (e.g. triethylamine, and the like) and a suitable reducing agent (e.g. sodium borohydride). The reaction proceeds at a temperature of about 0 to about 60° C. and can take up to about 48 hours to complete.

Compounds of Formula Ib, in which A is $R_5OC(O)$— and $R_3$ and $R_4$ are hydrogen, can be prepared by proceeding as in the following reaction scheme:

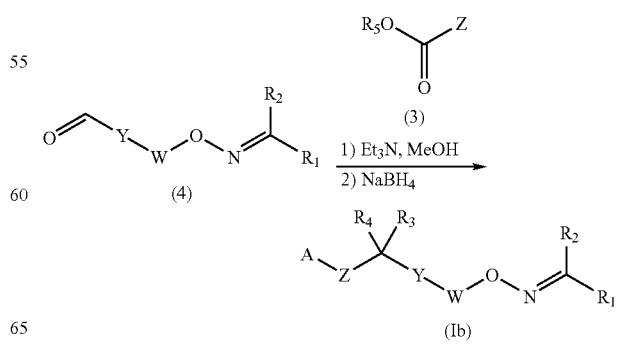

in which W, Y, Z, R$_1$, R$_2$, and R$_5$ are as defined for Formula Ib above. Compounds of Formula I can be prepared by reacting a compound of formula 4 with a compound of formula 3 in the presence of a suitable solvent (e.g. methanol, and the like), a suitable base (e.g. triethylamine, and the like) and a suitable reducing agent (e.g. sodium borohydride). The reaction proceeds at a temperature of about 0 to about 60° C. and can take up to about 48 hours to complete.

Additional Processes for Preparing Compounds of the Invention:

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T W. Greene, "Protecting Groups in Organic Chemistry", 3$^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferable, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from the their racemic mixture can be found in Jean Jacques, Andre Collet, Samuel H. Wilen, "Enantiomers, Racemates and Resolutions", John Wiley And Sons, Inc., 1981.

In summary, the compounds of Formula Ia or Ib can be made by a process, which involves:

(a) reacting a compound of formula 2 or 4 with a compound of formula 3; and (b) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The following examples provide detailed descriptions of the preparation of representative compounds and are offered to illustrate, but not to limit the present invention.

Example 1

3-{4-[1-(2-Trifluoromethyl-biphenyl-4-ylmethoxy-imino)-ethyl]-benzylamino}-propionic acid

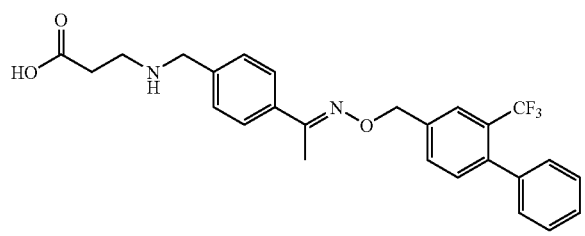

To a solution of 1-(4-hydroxymethyl-phenyl)-ethanone (1 eq) in methanol is added O-(4-chloro-3-trifluoromethyl-benzyl)-hydroxylamine (1 eq) followed by the addition of acetic acid (0.05 eq). The mixture is stirred at room temperature for 5 hours. After concentrated, the residue is purified by column chromatography (30% EtOAc in hexane) to give 1-(4-hydroxymethyl-phenyl)-ethanone O-(4-chloro-3-trifluoromethyl-benzyl)-oxime as an oil [MS: (ES+) 358.1 (M+1)+].

A mixture of 1-(4-hydroxymethyl-phenyl)-ethanone O-(4-chloro-3-trifluoromethyl-benzyl)-oxime (1 eq), phenyl boronic acid (1.5 eq), Pd(OAc)$_2$ (0.03 eq), phosphine ligand (0.06 eq) and KF (3 eq) in dry THF is heated at 100° C. in microwave for 30 minutes. The resulting mixture is diluted with EtOAc and washed with brine. The organic layer is dried over Na$_2$SO$_4$. After concentration, the residue is purified by column chromatography (30% EtOAc in hexane) to give 1-(4-hydroxymethyl-phenyl)-ethanone O-(2-trifluoromethyl-biphenyl-4-ylmethyl)-oxime as a white solid [MS: (ES+) 400.1 (M+1)+].

To a suspension of MnO$_2$ (10 eq) in dioxane is added 1-(4-hydroxymethyl-phenyl)-ethanone O-(2-trifluoromethyl-biphenyl-4-ylmethyl)-oxime (1 eq). The resulting mixture is refluxed for 10 minutes. After filtration and concentration, the residue is dissolved in MeOH and treated with β-alanine (2 eq) and Et$_3$N (1.5 eq). The resulting mixture is heated at 50° C. for 30 minutes. After cooling to room temperature, NaBH$_4$ (3 eq) is added in portions. Purification by preparative LCMS results in 3-{4-[1-(2-trifluoromethyl-biphenyl-4-ylmethoxyimino)-ethyl]-benzylamino}-propionic acid; $^1$H NMR (400 MHz, CD$_3$OD) δ 2.28 (s, 3H), 2.75 (t, J=6.8 Hz, 2H), 3.26 (t, J=6.8 Hz, 2H), 4.22 (s, 2H), 5.30 (s, 2H), 7.26-7.77 (m, 12H). MS: (ES+): 471.1 (M+1)+.

Example 2

3-{4-[1-(4-Cyclohexyl-3-trifluoromethyl-benzyloxyimino)-ethyl]-2-ethyl-benzylamino}-propionic acid

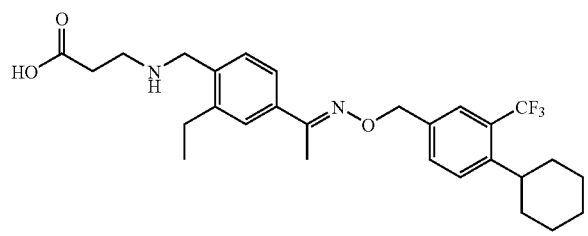

A mixture of 4-amino-3-ethyl-benzonitrile (5 mmol) and water (10 mL) is placed in a flask equipped with a magnetic stirrer and a thermometer probe. Concentrated hydrochloric acid (1.2 mL) is added slowly. After most of the solid is dissolved, ice (20 g) is added and the temperature is kept at 0° C. using an ice-salt bath. To the stirred mixture is added a solution of sodium nitrite (5 mmol) in water (2.5 mL), dropwise. The mixture is stirred at 0° C. for 30 minutes. A solution of hydrated sodium acetate in water is added to adjust the pH to neutral.

In a separate flask, a mixture of formaldoxime trimer hydrochloride (7.5 mmol), hydrated cupric sulfate (0.52 mmol), sodium sulfite (0.15 mmol) and a solution of sodium acetate (20 mmol) is prepared, and is cooled to 0° C.

The mixture of the diazonium salt is slowly added to the above mixture. After addition, the mixture is stirred at 0° C. for 1.5 hours, treated with concentrated hydrochloric acid (4.4 mL) and heated to reflux overnight.

The mixture is cooled to room temperature, and extracted with ethyl acetate. The combined ethyl acetate layers are washed with a saturated aqueous NaHCO$_3$, brine, dried over MgSO$_4$, and concentrated to give dark oil. 3-Ethyl-4-formyl-benzonitrile is isolated by column chromatography (EtOAc/Hexane gradient).

To a solution of 3-ethyl-4-formyl-benzonitrile (1.7 mmol) in ethanol (10 mL) at 0° C. is added NaBH$_4$ (1.7 mmol). The mixture is stirred at 0° C. for 0.5 hour, 5% citric acid (5 mL) is added and the solvent is removed under reduced pressure. The mixture is dissolved in EtOAc (50 mL), washed with saturated aqueous NaHCO$_3$, and brine. The separated organic layer is dried over MgSO$_4$, filtered and concentrated. 3-Ethyl-4-hydroxymethyl-benzonitrile is purified by column chromatography.

To a solution of 3-ethyl-4-hydroxymethyl-benzonitrile (1.21 mmol) in dry THF under N$_2$ is added methyl magnesium bromide (3.63 mmol, 3.0 M in diethyl ether). The mixture is heated to reflux overnight. The mixture is cooled, concentrated HCl (10 mL) is added and the mixture is extracted with EtOAc. The combined EtOAc layers are washed with saturated aqueous NaHCO$_3$ and brine. The organic layer is separated, dried over MgSO$_4$, filtered and concentrated. The crude product 1-(3-ethyl-4-hydroxymethyl-phenyl)-ethanone is carried to the next step without further purification.

To a solution of 1-(3-ethyl-4-hydroxymethyl-phenyl)-ethanone (1 eq) in methanol is added O-(4-cyclohexyl-3-trifluoromethyl-benzyl)-hydroxylamine (1 eq) followed by the addition of acetic acid (0.05 eq). The mixture is stirred at room temperature for 12 hours. After concentration, the residue is purified by column chromatography (30% EtOAc in hexane) to give 1-(3-ethyl-4-hydroxymethyl-phenyl)-ethanone O-(4-cyclohexyl-3-trifluoromethyl-benzyl)-oxime as an oil [MS: (ES+) 434.2 (M+1)+].

To a suspension of MnO$_2$ (10 eq) in dioxane is added 1-(3-ethyl-4-hydroxymethyl-phenyl)-ethanone O-(4-cyclohexyl-3-trifluoromethyl-benzyl)-oxime (1 eq). The resulting mixture is refluxed for 10 minutes. After filtration and concentration, the residue is dissolved in MeOH and treated with P-alanine (2 eq) and Et$_3$N (1.5 eq). The resulting mixture is heated at 50° C. for 30 minutes. After cooling to room temperature, NaBH$_4$ (3 eq) is added in portions. Purification by preparative LCMS results in 3-{4-[1-(4-cyclohexyl-3-trifluoromethyl-benzyloxyimino)-ethyl]-2-ethyl-benzylamino}-propionic acid; $^1$H NMR (400 MHz, CD$_3$OD) δ 1.25 (t, 3H), 1.45 (m, 5H), 1.85 (m, 5H), 2.28 (s, 3H), 2.79 (m, 4H), 2.95 (m, 1H), 3.36 (t, 2H), 4.31 (s, 2H), 5.26 (s, 2H) 7.42-7.68 (m, 6H). MS: (ES+): 505.3 (M+1)+.

Example 3

1-{4-[1-(4-Cyclohexyl-3-trifluoromethyl-benzyloxyimino)-ethyl]-2-ethyl-benzyl}-azetidine-3-carboxylic acid

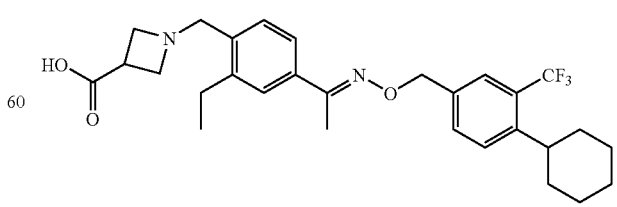

To a suspension of MnO$_2$ (10 eq) in dioxane is added 1-(3-ethyl-4-hydroxymethyl-phenyl)-ethanone O-(4-cyclohexyl-3-trifluoromethyl-benzyl)-oxime (1 eq). The resulting mixture is refluxed for 10 minutes. After filtration and concentration, the residue is dissolved in MeOH and treated with azetidine-3-carboxylic acid (2 eq) and Et$_3$N (1.5 eq). The resulting mixture is heated at 50° C. for 30 minutes. After cooling to room temperature, NaBH$_3$CN (3 eq) is added in portions. Purification by preparative LCMS results in 1-{4-[1-(4-cyclohexyl-3-trifluoromethyl-benzyloxyimino)-ethyl]-2-ethyl-benzyl}-azetidine-3-carboxylic acid; $^1$H NMR (400 MHz, CD$_3$OD) δ 1.24 (t, 3H), 1.30-1.60 (m, 5H), 1.74-1.92 (m, 5H), 2.28 (s, 3H), 2.79 (q, 2H), 2.92 (m, 1H), 3.68 (m, 1H), 4.32 (m, 4H), 4.51 (s, 2H) 5.22 (s, 2H), 7.38 (d, 1H), 7.50-7.68 (m, 5H). MS: (ES$^+$): 517.3 (M+1)$^+$.

Example 4

3-({2-Chloro-6-[1-(4-cyclohexyl-3-trifluoromethyl-benzyloxyimino)-ethyl]-pyridin-3-ylmethyl}-amino)-propionic acid

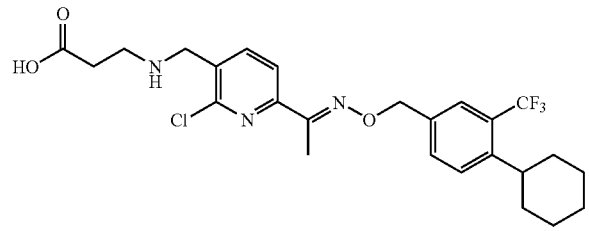

To a solution of 1-(6-chloro-5-methyl-pyridin-2-yl)-ethanone (1 eq) in CCl$_4$ is added NBS (1 eq) and BPO (0.1 eq). The mixture is refluxed for 12 hours. After concentration, 1-(5-bromomethyl-6-chloro-pyridin-2-yl)-ethanone is isolated by flash column chromatography. MS: (ES$^+$): 247.9 (M+1)$^+$.

To a solution of 3-amino-propionic acid tert-butyl ester hydrochloride (1.5 eq) in DMF is added NaH (3.5 eq). The resulting mixture is stirred at room temperature for 15 minutes and a solution of 1-(5-bromomethyl-6-chloro-pyridin-2-yl)-ethanone (1 eq) in DMF is then added. After stirring for 3 hours, it is partitioned with 20% EtOAc/hexane and H$_2$O. The organic layer is washed with brine and dried. After concentration, 3-[(6-acetyl-2-chloro-pyridin-3-ylmethyl)-amino]-propionic acid tert-butyl ester is isolated by flash column chromatography. MS: (ES$^+$): 313.1 (M+1)$^+$.

To a solution of 3-[(6-acetyl-2-chloro-pyridin-3-ylmethyl)-amino]-propionic acid tert-butyl ester (1 eq) in methanol is added O-(4-chloro-3-trifluoromethyl-benzyl)-hydroxylamine (1 eq) followed by the addition of acetic acid (0.05 eq). The mixture is stirred at room temperature for 5 hours. After concentration, the residue is purified by column chromatography to give 3-({2-chloro-6-[1-(4-cyclohexyl-3-trifluoromethyl-benzyloxyimino)-ethyl]-pyridin-3-ylmethyl}-amino)-propionic acid tert-butyl ester. MS: (ES$^+$) 568.3 (M+1)$^+$. The tert-butyl group is subsequently removed by treatment with TFA/DCM (1/1) at room temperature. The final compound 3-({2-chloro-6-[1-(4-cyclohexyl-3-trifluoromethyl-benzyloxyimino)-ethyl]-pyridin-3-ylmethyl}-amino)-propionic acid is purified by preparative LCMS. $^1$H NMR (400 MHz, CD$_3$OD) δ 1.28-1.60 (m, 5H), 1.71-1.92 (m, 5H), 2.30 (s, 3H), 2.79 (t, 2H), 2.90 (m, 1H), 3.38 (t, 2H), 4.42 (s, 2H), 5.29 (s, 2H), 7.38 (d, 1H), 7.50-7.68 (m, 3H), 7.94 (s, 2H). MS: (ES$^+$): 512.2 (M+1)$^+$.

Example 5

3-({6-[1-(4-Cyclohexyl-3-trifluoromethyl-benzyloxyimino)-ethyl]-2-ethyl-pyridin-3-ylmethyl}-amino)-propionic acid

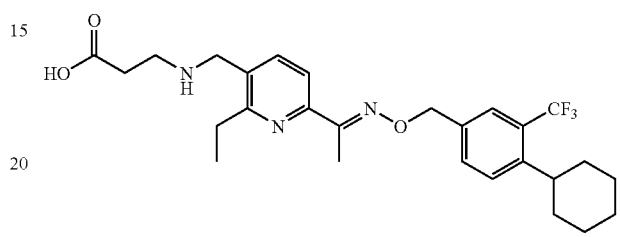

A mixture of 3-[(6-acetyl-2-chloro-pyridin-3-ylmethyl)-amino]-propionic acid tert-butyl ester (1 eq), tributyl-vinyltin (1.2 eq), Pd(PPh$_3$)$_4$ (0.05 eq), and LiCl (3 eq) in dioxane is heated at 100° C. for 12 hours. The reaction mixture is diluted with EtOAc and stirred together with aqueous KF for 10 minutes. It is then filtered through celite and the organic layer is washed with brine. After concentration, the residue is purified by flash column chromatography to give 3-[(6-cetyl-2-vinyl-pyridin-3-ylmethyl)-amino]-propionic acid tert-butyl ester. MS: (ES$^+$): 305.2 (M+1)$^+$.

The above compound is dissolved in EtOH and hydrogenated in the presence of 10% Pd—C. After filtration and concentration, the crude product 3-[(6-acetyl-2-ethyl-pyridin-3-ylmethyl)-amino]-propionic acid tert-butyl ester is used directly in the next step without further purification.

To a solution of 3-[(6-acetyl-2-ethyl-pyridin-3-ylmethyl)-amino]-propionic acid tert-butyl ester (1 eq) in methanol is added O-(4-chloro-3-trifluoromethyl-benzyl)-hydroxylamine (1 eq) followed by the addition of acetic acid (0.05 eq). The mixture is stirred at room temperature for 5 hours. After concentration, the residue is purified by column chromatography to give 3-({6-[1-(4-cyclohexyl-3-trifluoromethyl-benzyloxyimino)-ethyl]-2-ethyl-pyridin-3-ylmethyl}-amino)-propionic acid tert-butyl ester. MS: (ES$^+$) 562.3 (M+1)$^+$. The tert-butyl group is subsequently removed by treatment with TFA/DCM (1/1) at room temperature. The final compound 3-({6-[1-(4-cyclohexyl-3-trifluoromethyl-benzyloxyimino)-ethyl]-2-ethyl-pyridin-3-ylmethyl}-amino)-propionic acid is purified by preparative LCMS. $^1$H NMR (400 MHz, CD$_3$OD) δ 1.30-1.62 (m, 8H), 1.72-1.91 (m, 5H), 2.36 (s, 3H), 2.78 (t, 2H), 2.94 (m, 3H), 3.37 (t, 2H), 4.42 (s, 2H), 5.29 (s, 2H), 7.51-7.80 (m, 5H). MS: (ES$^+$): 506.3 (M+1)$^+$.

By repeating the procedure described in the above examples, using appropriate starting materials, the following compounds of Formula Ia or Ib can be synthesized (Table 1).

TABLE 1
| Compound | Structure | Physical Data MS ES (M + 1) |
|---|---|---|
| 6 | 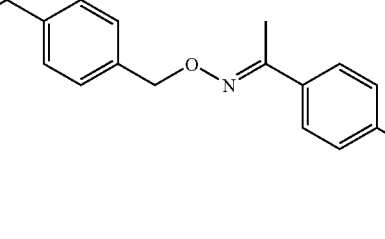 | 403.2 |
| 7 | 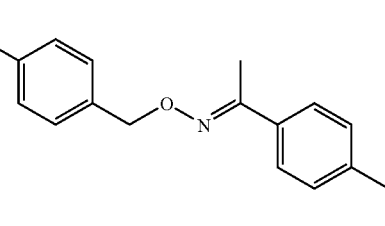 | 417.2 |
| 8 | 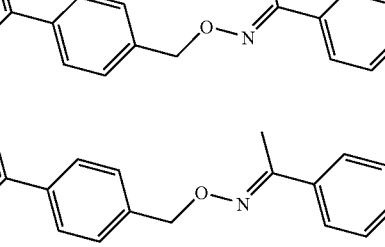 | 415.2 |
| 9 | 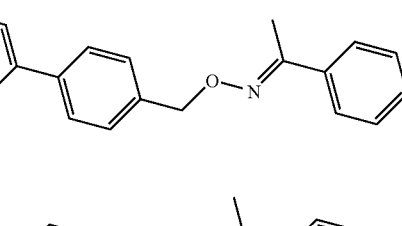 | 443.2 |
| 10 | 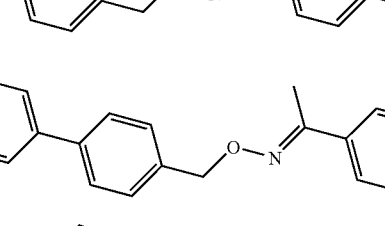 | 389.2 |
| 11 | 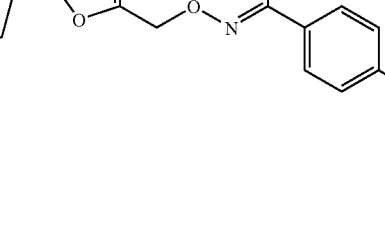 | 443.2 |
| 12 | 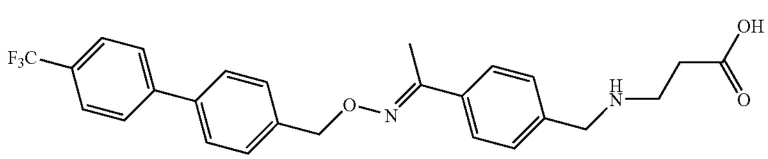 | 471.2 |
| 13 | 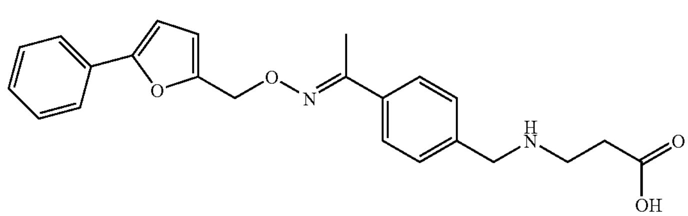 | 393.2 |

TABLE 1-continued

| Compound | Structure | Physical Data MS ES (M + 1) |
|---|---|---|
| 14 | (3-trifluoromethylbiphenyl-4-yl)methyl oxime structure | 471.2 |
| 15 | (3-trifluoromethyl-biphenyl)methyl oxime structure | 471.2 |
| 16 | (4-methoxybiphenyl-4-yl)methyl oxime structure | 433.2 |
| 17 | (biphenyl-3-yl)methyl oxime structure | 403.2 |
| 18 | (4-(thiophen-2-yl)phenyl)methyl oxime structure | 409.2 |
| 19 | (3-trifluoromethyl-4-(thiophen-2-yl)phenyl)methyl oxime structure | 477.2 |

TABLE 1-continued

| Compound | Structure | Physical Data MS ES (M + 1) |
|---|---|---|
| 20 | 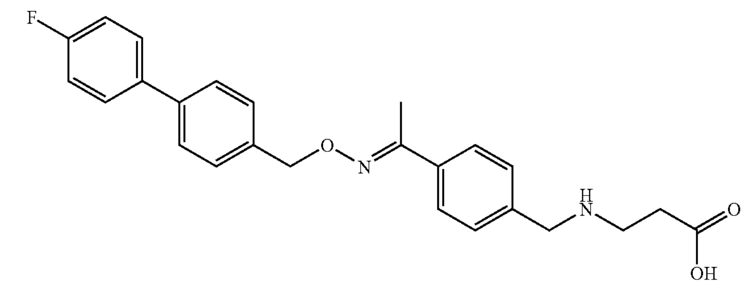 | 421.1 |
| 21 | 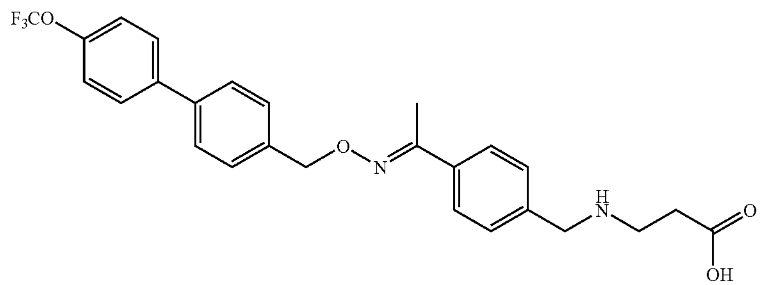 | 487.2 |
| 22 | 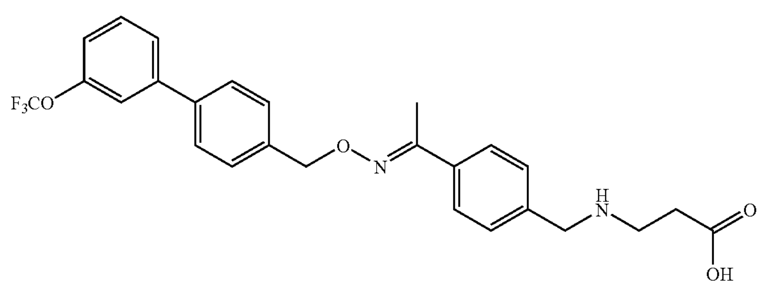 | 487.2 |
| 23 | 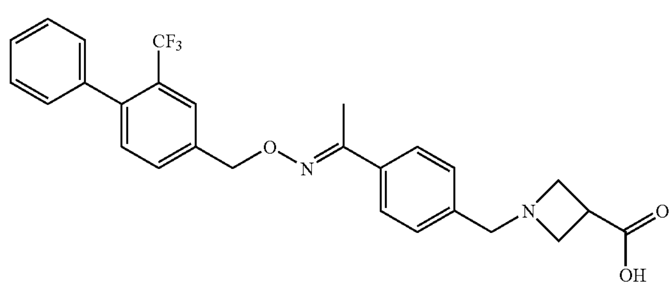 | 483.1 |
| 24 | 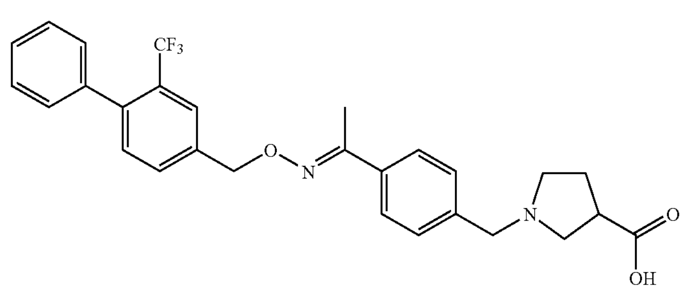 | 497.2 |

TABLE 1-continued

| Compound | Structure | Physical Data MS ES (M + 1) |
|---|---|---|
| 25 | 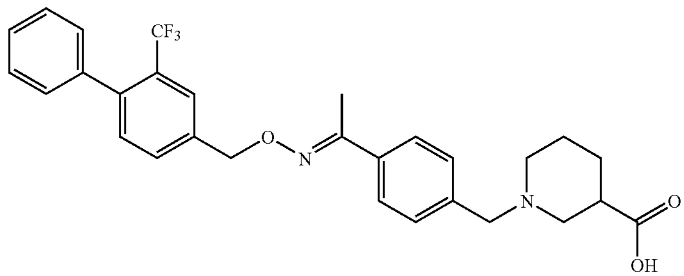 | 511.2 |
| 26 | 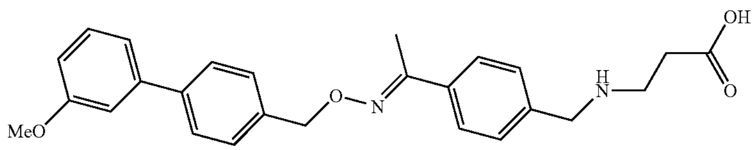 | 433.2 |
| 27 | 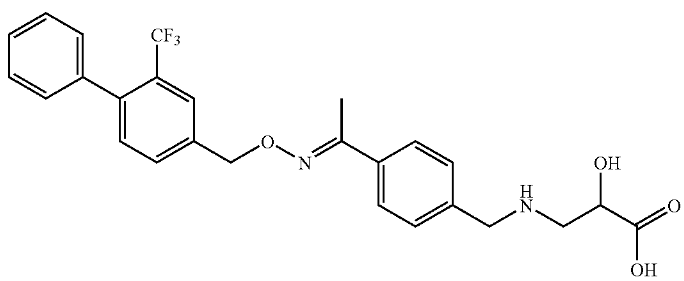 | 31.9 |
| 28 | 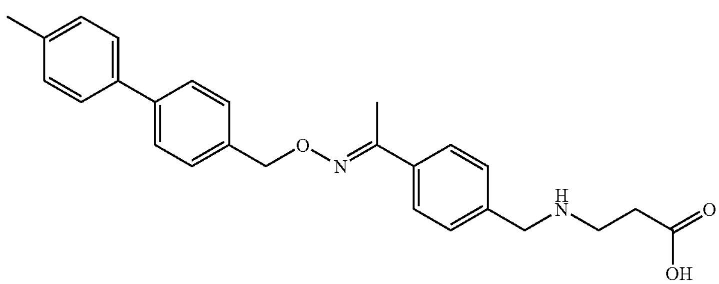 | 417.2 |
| 29 | 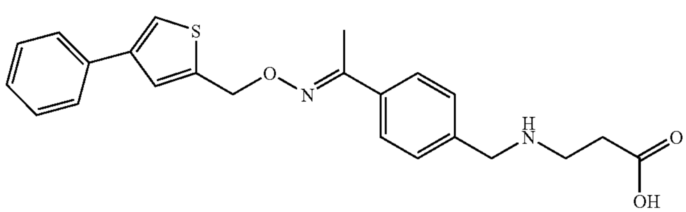 | 409.2 |
| 30 | 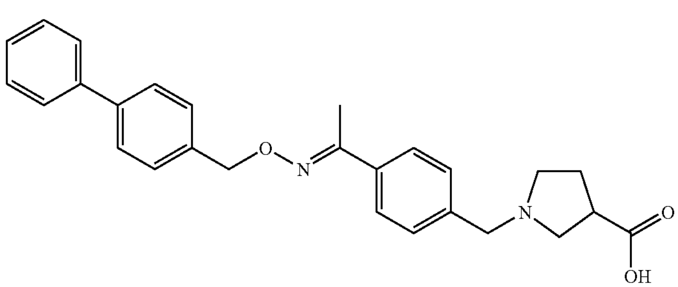 | 429.2 |

TABLE 1-continued

| Compound | Structure | Physical Data MS ES (M + 1) |
|---|---|---|
| 31 | 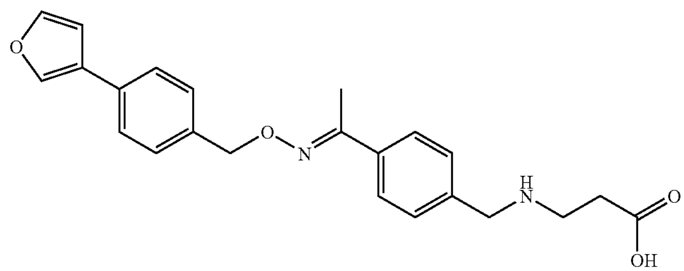 | 393.2 |
| 32 | 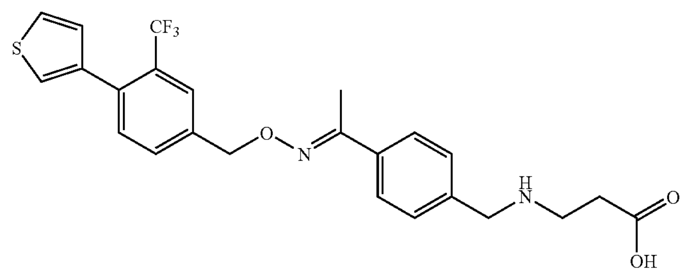 | 477.2 |
| 33 | 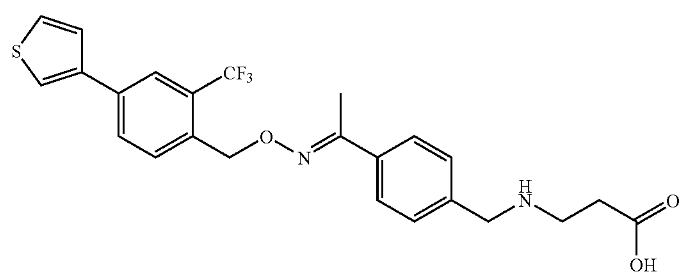 | 477.2 |
| 34 | 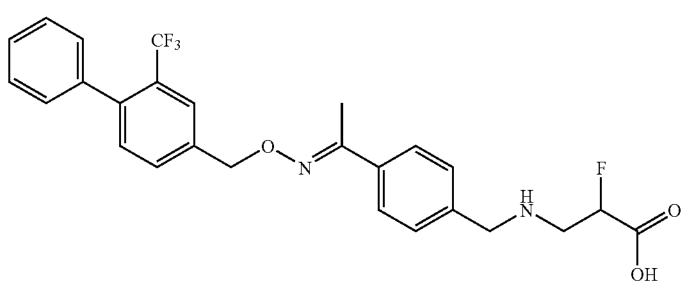 | 489.2 |
| 35 | 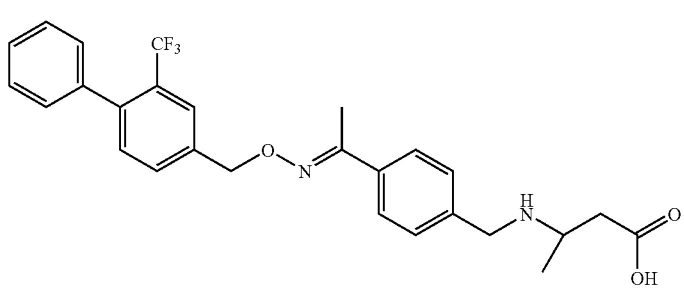 | 485.2 |

TABLE 1-continued

| Compound | Structure | Physical Data MS ES (M + 1) |
|---|---|---|
| 36 | 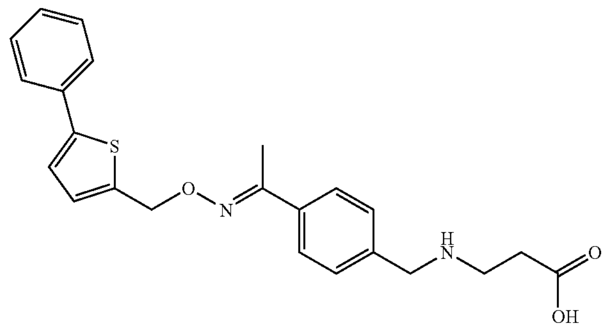 | 409.2 |
| 37 | 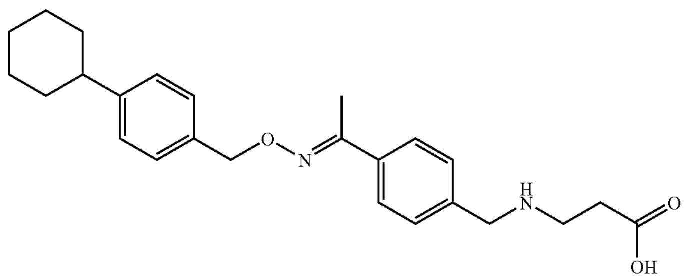 | 409.2 |
| 38 | 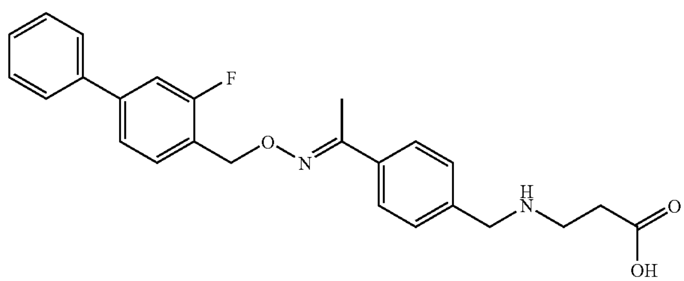 | 421.2 |
| 39 | 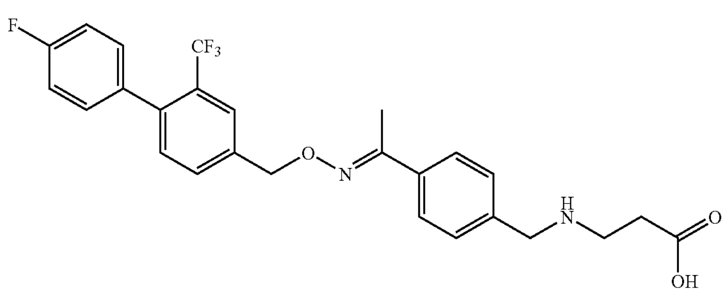 | 489.2 |
| 40 | 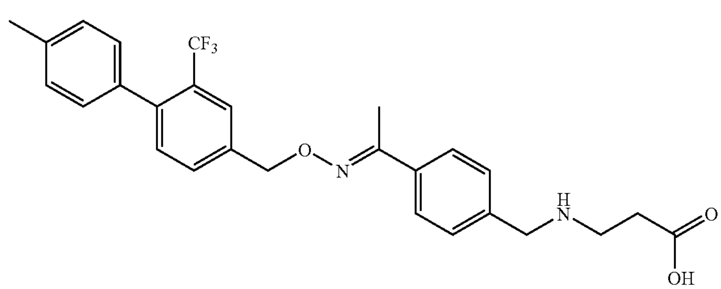 | 485.2 |

TABLE 1-continued

| Compound | Structure | Physical Data MS ES (M + 1) |
|---|---|---|
| 41 | 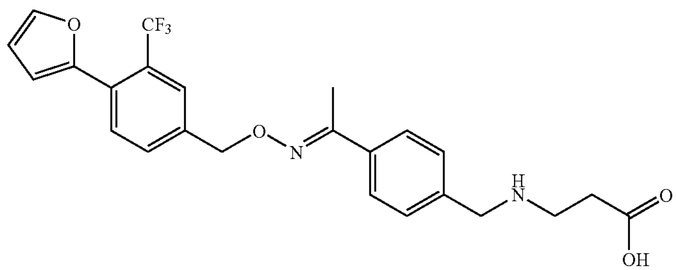 | 461.2 |
| 42 | 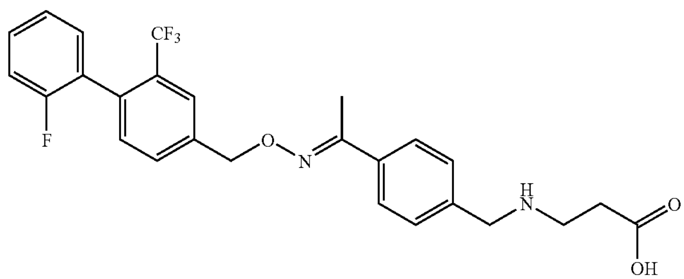 | 489.2 |
| 43 | 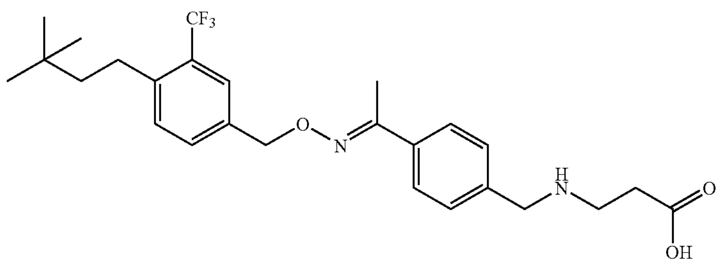 | 479.2 |
| 44 | 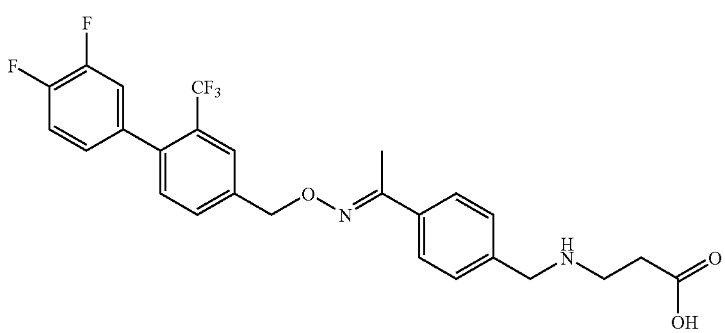 | 507.2 |
| 45 | 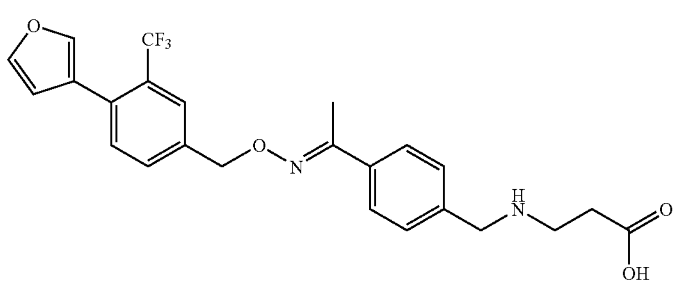 | 461.2 |

TABLE 1-continued

| Compound | Structure | Physical Data MS ES (M + 1) |
|---|---|---|
| 46 | 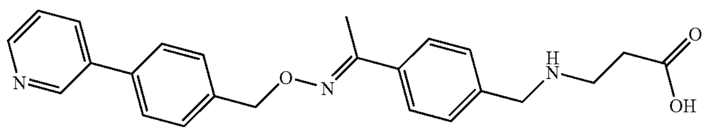 | 404.2 |
| 47 | 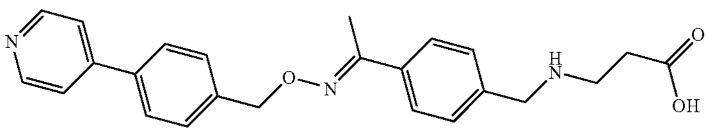 | 404.2 |
| 48 | 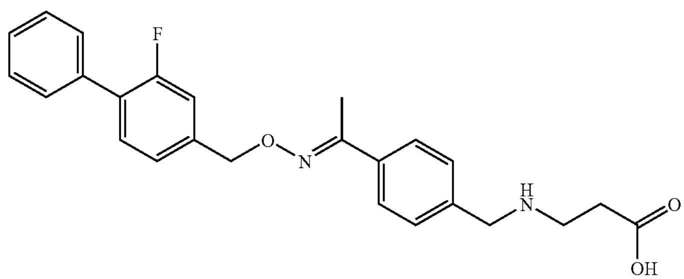 | 421.2 |
| 49 | 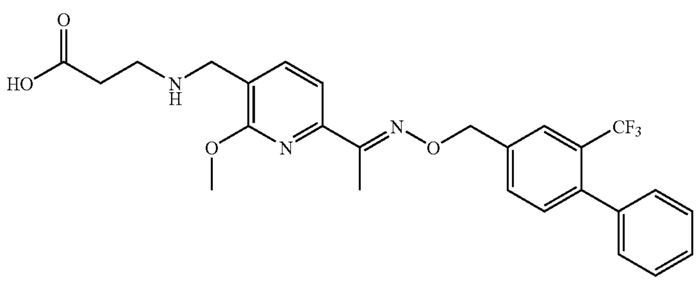 | 502.2 |
| 50 | 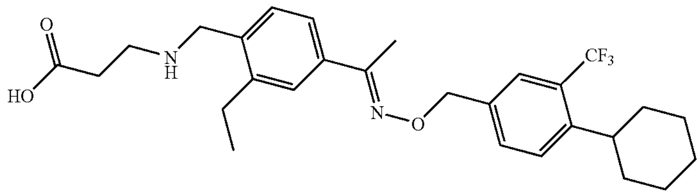 | 505.3 |
| 51 | 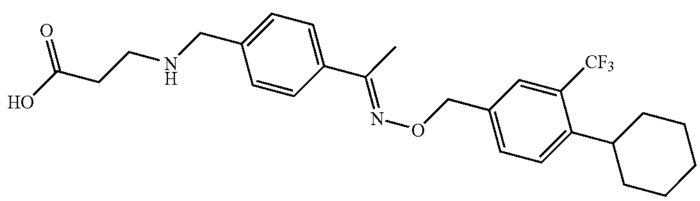 | 477.2 |
| 52 | 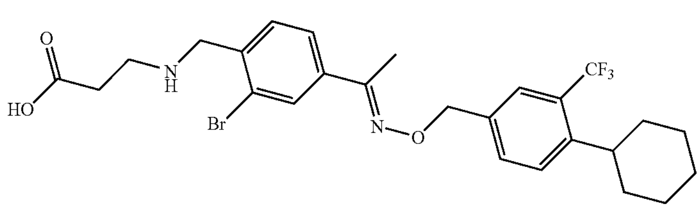 | 555.1 |

TABLE 1-continued

| Compound | Structure | Physical Data MS ES (M + 1) |
|---|---|---|
| 53 | 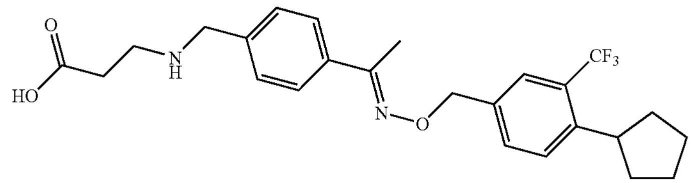 | 463.2 |
| 54 | 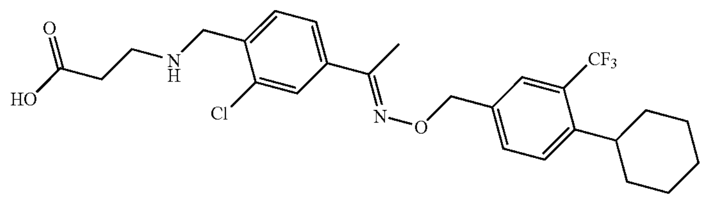 | 511.2 |
| 55 | 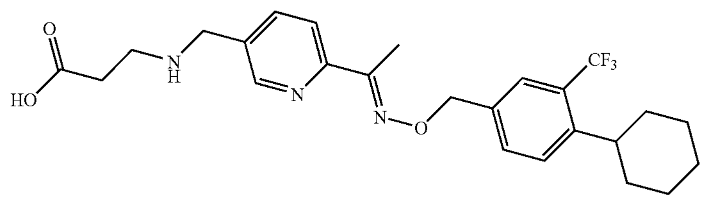 | 478.2 |
| 56 | 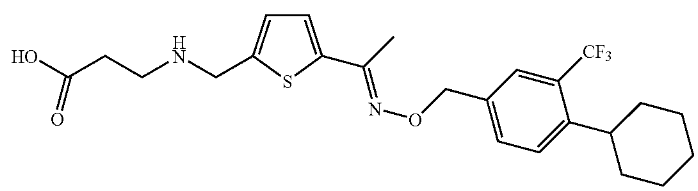 | 483.2 |
| 57 | 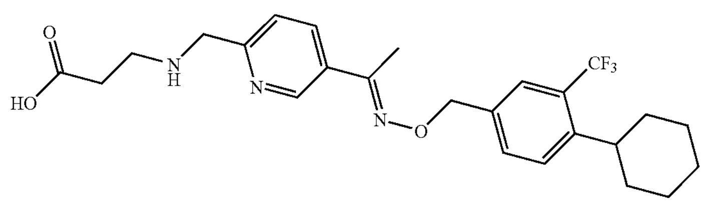 | 478.2 |
| 58 | 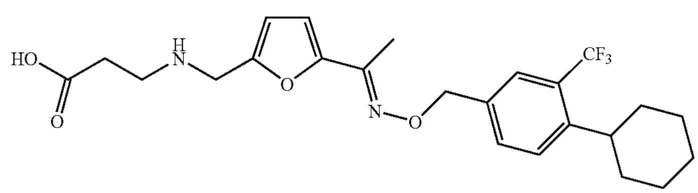 | 467.2 |
| 59 | 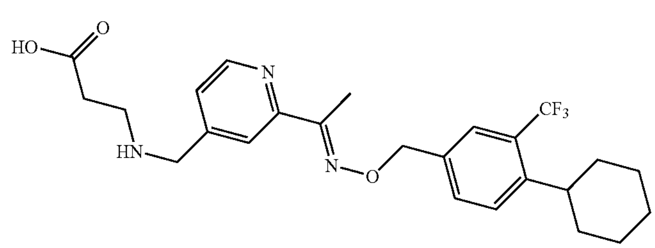 | 478.2 |

TABLE 1-continued
| Compound | Structure | Physical Data MS ES (M + 1) |
|---|---|---|
| 60 | 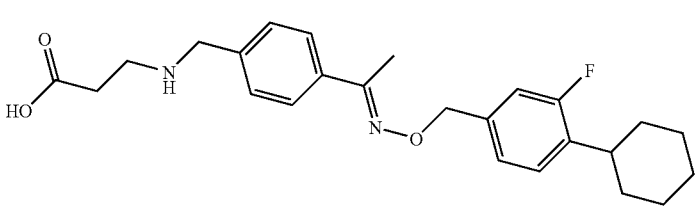 | 427.2 |
| 61 | 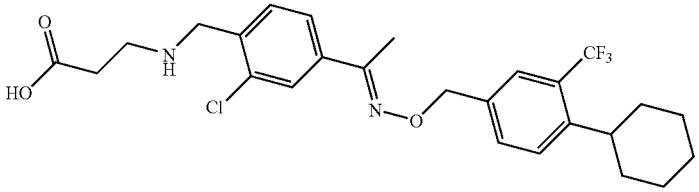 | 512.2 |
| 62 | 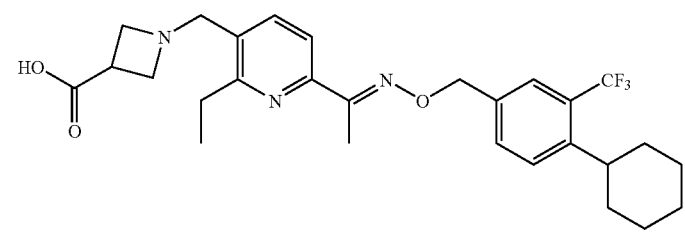 | 518.3 |
| 63 | 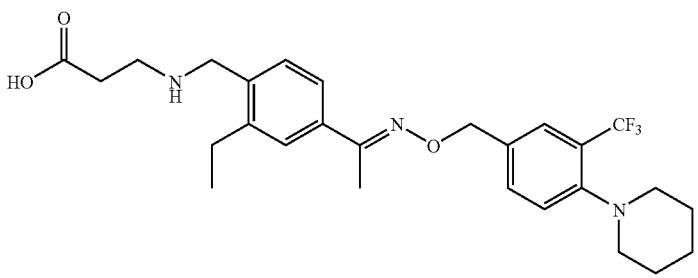 | 506.3 |
| 64 | 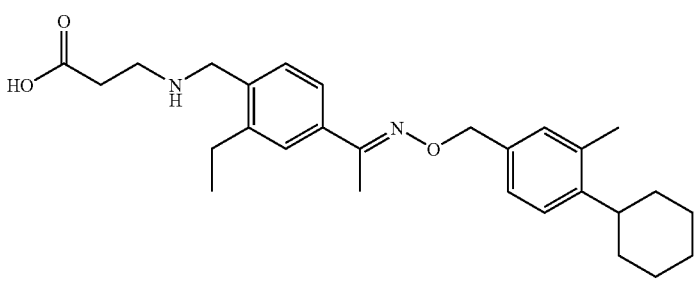 | 451.3 |
| 65 | 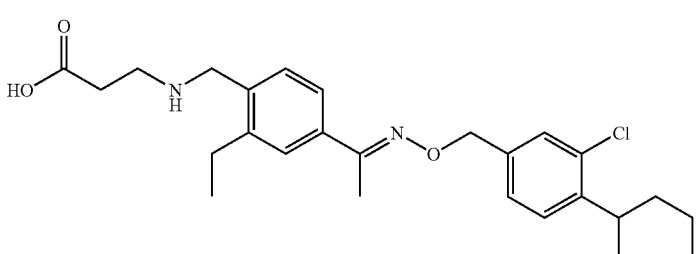 | 471.2 |

TABLE 1-continued
| Compound | Structure | Physical Data MS ES (M + 1) |
|---|---|---|
| 66 | 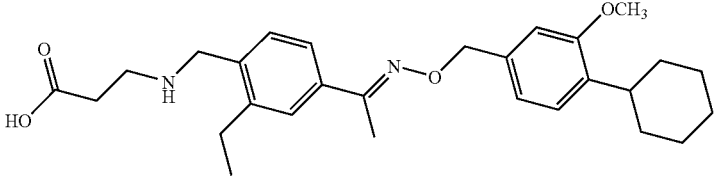 | 467.3 |
| 67 | 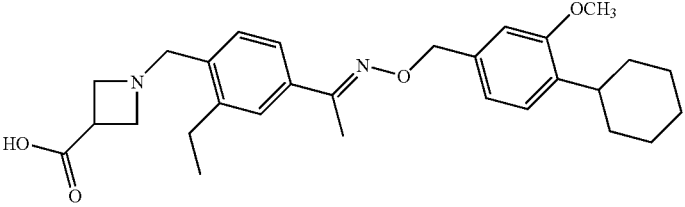 | 479.3 |
| 68 | 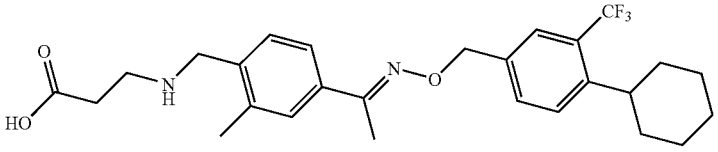 | 491.3 |
| 69 | 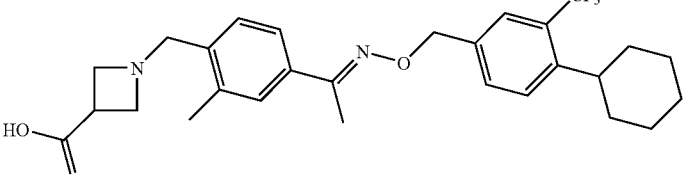 | 503.2 |
| 70 | 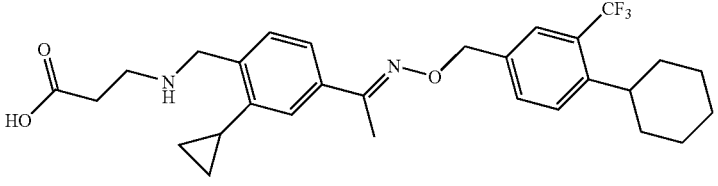 | 517.3 |
| 71 | 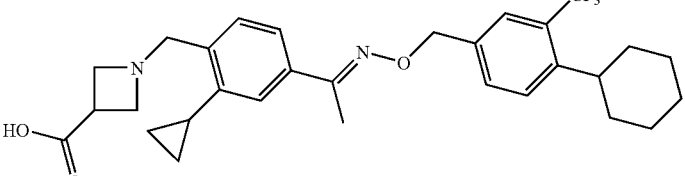 | 529.3 |
| 72 | 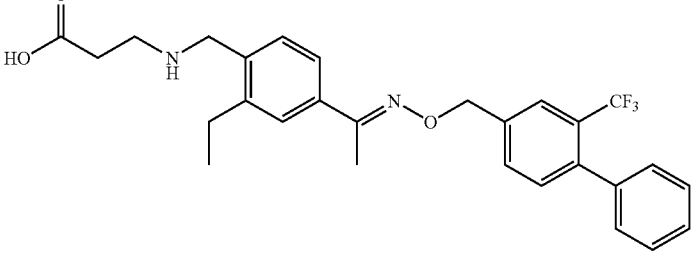 | 499.2 |

TABLE 1-continued

| Compound | Structure | Physical Data MS ES (M + 1) |
|---|---|---|
| 73 | 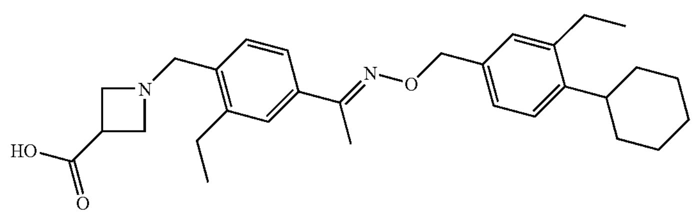 | 477.3 |
| 74 | 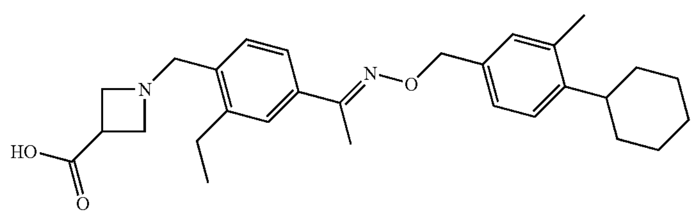 | 463.3 |
| 75 | 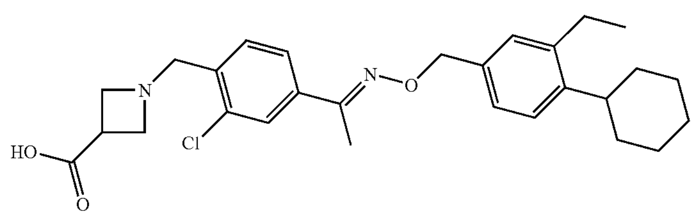 | 483.2 |
| 76 | 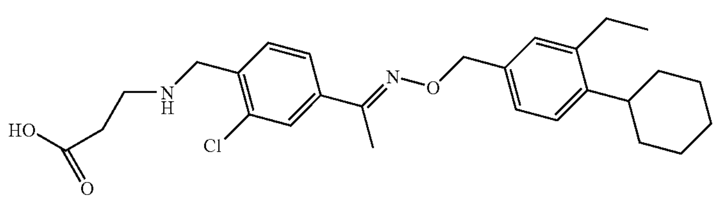 | 471.2 |
| 77 | 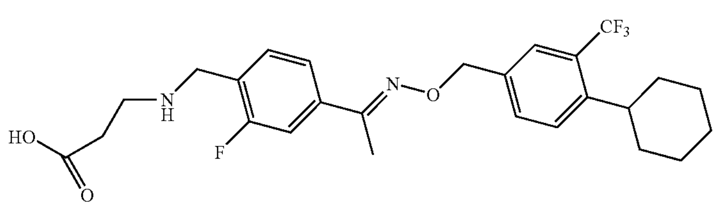 | 495.2 |
| 78 | 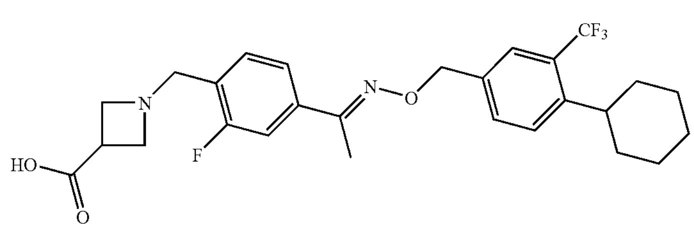 | 507.2 |
| 79 | 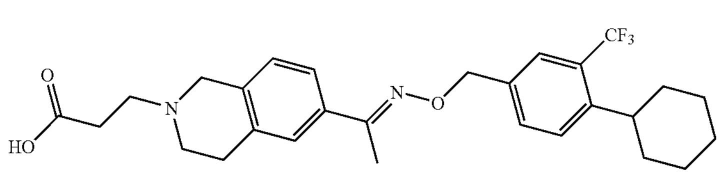 | 503.2 |

TABLE 1-continued

| Compound | Structure | Physical Data MS ES (M + 1) |
|---|---|---|
| 80 | [structure] | 463.3 |
| 81 | [structure] | |
| 82 | [structure] | |
| 83 | [structure] | |
| 84 | [structure] | |
| 85 | [structure] | |

Example 6

Compounds of Formula Ia or Ib Exhibit Biological Activity

A. In Vitro: GPCR Activation Assay Measuring GTP [γ-$^{35}$S] Binding to Membranes Prepared from Cho Cells Expressing Human EDG Receptors EDG-1 (S1P$_1$) GTP [γ-$^{35}$S] binding assay: Homogenized membranes are prepared from CHO cell clones stably expressing a human EDG-1 N-terminal c-myc tag. Cells are grown in suspension in two 850 cm$^2$ roller bottles for three or fours days before harvesting. The cells are centrifuged down, washed once with cold PBS, and resuspended in ≦20 ml of Buffer A (20 mM HEPES, pH 7.4, 10 mM EDTA, EDTA-free complete protease inhibitor cocktail [1 tablet/25 ml]). The cell suspension is homogenized on ice, using a Polytron homogenizer at 30000 rpm at three intervals of 15 seconds each. The homogenate is first centrifuged at 2000 rpm on a tabletop low speed centrifuge for 10 minutes. The supernatant, after passing through a cell strainer, is then re-centrifuged at 50,000×g for 25 minutes at 4° C. The pellet is resuspended into buffer B (15% glycerol, 20 mM HEPES, pH 7.4, 0.1 mM EDTA, EDTA-free complete protease inhibitor cocktail [1 tablet/10 ml]). Protein concentration of the prep is determined using the BCA Protein Assay kit (Pierce) using BSA as standard. The membranes are aliquoted and kept frozen at −80° C.

Solutions of test compounds ranging from 10 mM to 0.01 nM are prepared in DMSO. S1P is diluted in 4% BSA solution as positive controls. The desired amount of membrane prep is diluted with ice-cold assay buffer (20 mM HEPES, pH 7.4, 100 mM NaCl, 10 mM $MgCl_2$, 0.1% Fatty acid-free BSA, 5 µM GDP) and vortexed well. 2 µl or less of compound is distributed into each well of a round-bottom 96-well polystyrene assay plate, followed by addition of 100 µl of diluted membranes (3-10 µg/well) and kept on ice until the addition of hot GTPγS. [$^{35}$S]-GTPγS is diluted 1:1000 (v/v) with cold assay buffer and 100 µl is added into each well. The reaction is carried out at room temperature for 90 minutes before the membranes are harvested onto Perkin-Elmer Unifilter® GF/B-96 filter plate using a Packard Filtermate Harvester. After several washes with wash buffer (20 mM HEPES, pH 7.4, 100 mM NaCl, 10 mM $MgCl_2$), and a rinse with 95% ethanol, the filter is dried in a 37° C. oven for 30 minutes. MicroScint-20 is added and the plate sealed for scintillation counting on TopCount. EC50 values are obtained by fitting the GTP [γ-$^{35}$S] binding curves (raw data) with the dose response curve-fitting tool of GraphPad Prism. Six or twelve different concentrations are used to generate a concentration response curve (using three data points per concentration).

EDG-3, -5, -6 and -8 GTP [γ-$^{35}$S] binding assays are carried out in a comparable manner to the EDG-1 GTP [γ-$^{35}$S] binding assay using membranes from CHO cells stably expressing c-terminal c-myc tagged or untagged receptors. For each membrane preparation, titration experiments are first run with S1P control to determine the optimal amount of membranes to be added per assay well. Compounds of the invention were tested according to the above assay and were observed to exhibit selectivity for the EDG-1 receptor. For example, 3-{4-[1-(4-cyclohexyl-3-trifluoromethyl-benzyloxyimino)-ethyl]-2-ethyl-benzylamino}-propionic acid (example 2) has an $EC_{50}$ of 0.8 nM in the above assay and is at least 1000 fold selective for EDG-1 compared to one or more of the other receptors including EDG-3, EDG-5, EDG-6 and EDG-8. Similarly, 1-{4-[1-(4-Cyclohexyl-3-trifluoromethyl-benzyloxyimino)-ethyl]-2-ethyl-benzyl}-azetidine-3-carboxylic acid (example 3) has an $EC_{50}$ of 0.2 nM in the above assay and is at least 1000 fold selective for EDG-1 compared to one or more of the other receptors including EDG-3, EDG-5, EDG-6 and EDG-8.

B. In Vitro: FLIPR Calcium Flux Assay

Compounds of the invention are tested for agonist activity on EDG-1, EDG-3, EDG-5, and EDG-6 with a FLIPR calcium flux assay. Briefly, CHO cells expressing an EDG receptor are maintained in F-12K medium (ATCC), containing 5% FBS, with 500 ug/ml of G418. Prior to the assay, the cells are plated in 384 black clear bottom plates at the density of 10,000 cells/well/25 µl in the medium of F-12K containing 1% FBS. The second day, the cells are washed three times (25 µl/each) with washing buffer. About 25 µl of dye are added to each well and incubated for 1 hour at 37° C. and 5% $CO_2$. The cells are then washed four times with washing buffer (25 µl/each). The calcium flux is assayed after adding 25 µl of SEQ2871 solution to each well of cells. The same assay is performed with cells expressing each of the different EDG receptors. Titration in the FLIPR calcium flux assay is recorded over a 3-minute interval, and quantitated as maximal peak height percentage response relative to EDG-1 activation.

C. In Vivo: Screening Assays for Measurement of Blood Lymphocyte Depletion and Assessment of Heart Effect Measurement of circulating lymphocytes: Compounds are dissolved in DMSO and diluted to obtain a final concentration of 4% DMSO (v/v, final concentration) and then further diluted in a constant volume of Tween80 25%/H2O, v/v. Tween80 25%/H2O (200 µl), 4% DMSO, and FTY720 (10 µg) are included as negative and positive controls, respectively. Mice (C57bl/6 male, 6-10 week-old) are administered 250-300 µL of compound solution orally by gavages under short isoflurane anesthesia.

Blood is collected from the retro-orbital sinus 6 and 24 hours after drug administration under short isoflurane anesthesia. Whole blood samples are subjected to hematology analysis. Peripheral lymphocyte counts are determined using an automated analyzer. Subpopulations of peripheral blood lymphocytes are stained by fluorochrome-conjugated specific antibodies and analyzed using a fluorescent activating cell sorter (Facscalibur). Two mice are used to assess the lymphocyte depletion activity of each compound screened. The result is an $ED_{50}$, which is defined as the effective dose required displaying 50% of blood lymphocyte depletion. Compounds of the invention were tested according to the above assay and were preferably found to exhibit an $ED_{50}$ of less than 1 mg/kg, more preferably an $ED_{50}$ of less than 0.5 mg/kg. For example, 3-{4-[1-(4-cyclohexyl-3-trifluoromethyl-benzyloxyimino)-ethyl]-2-ethyl-benzylamino}-propionic acid (example 2) exhibits an ED50 of 0.07 mg/kg. Further, 1-{4-[1-(4-Cyclohexyl-3-trifluoromethyl-benzyloxyimino)-ethyl]-2-ethyl-benzyl}-azetidine-3-carboxylic acid (example 3) exhibits and ED50 of 0.1 mg/kg.

Assessment of Heart Effect: The effects of compounds on cardiac function are monitored using the AnonyMOUSE ECG screening system. Electrocardiograms are recorded in conscious mice (C57bl/6 male, 6-10 week-old) before and after compound administration. ECG signals are then processed and analyzed using the e-MOUSE software. 90 µg of compound further diluted in 200 µl water, 15% DMSO are injected IP. Four mice are used to assess the heart effect of each compound.

D: In Vivo: Anti-Angiogenic Activity

Porous chambers containing (i) sphingosine-1-phosphate (5 µM/chamber) or (ii) human VEGF (1 µg/chamber) in 0.5 ml of 0.8% w/v agar (containing heparin, 20 U/ml) are implanted subcutaneously in the flank of mice. S1P or VEGF induces the growth of vascularized tissue around the chamber. This response is dose-dependent and can be quantified by measuring the weight and blood content of the tissue. Mice are treated once a day orally or intravenously with a compound of Formula Ia or Ib starting 4-6 hours before implantation of the chambers and continuing for 4 days. The animals are sacrificed for measurement of the vascularized tissues 24 hours after the last dose. The weight and blood content of the vascularized tissues around the chamber is determined. Animals treated with a compound of Formula Ia or Ib show reduced weight and/or blood content of the vascularized tissues compared to animals treated with vehicle alone. Compounds of Formula Ia or Ib are anti-angiogenic when administered at a dose of about 0.3 to about 3 mg/kg.

E: In Vitro: Antitumor Activity

A mouse breast cancer cell line originally isolated from mammary carcinomas is used, e.g. JygMC(A). The cell number is adjusted to 5×10$^5$ for plating in fresh medium before the procedure. Cells are incubated with fresh medium containing 2.5 mM of thymidine without FCS for 12 hours and then washed twice with PBS, followed by addition of fresh medium with 10% FCS and additionally incubated for another 12 hours. Thereafter the cells are incubated with fresh medium containing 2.5 mM of thymidine without FCS for 12 hours. To release the cells from the block, the cells are washed twice with PBS and replated in fresh medium with 10% FCS. After synchronization, the cells are incubated with or without various concentrations of a compound of Formula Ia or Ib for 3, 6, 9, 12, 18 or 24 hours. The cells are harvested after treatment with 0.2% EDTA, fixed with ice-cold 70% ethanol solution, hydrolyzed with 250 µg/ml of RNaseA (type 1-A: Sigma Chem. Co.) at 37° C. for 30 minutes and stained with propidium iodide at 10 mg/ml for 20 minutes. After the incubation period, the number of cells is determined both by counting cells in a Coulter counter and by the SRB colorimetric assay. Under these conditions compounds of Formula Ia or Ib inhibit the proliferation of the tumor cells at concentrations ranging from $10^{-12}$ to $10^{-6}$ M.

It is understood that the examples and embodiments described herein are for illustrative purposes only and that various modifications or changes in light thereof will be suggested to persons skilled in the art and are to be included within the spirit and understanding of this application and scope of the appended claims. All publications, patents, and patent applications cited herein are hereby incorporated by reference for all purposes.

We claim:
1. A compound of the formula

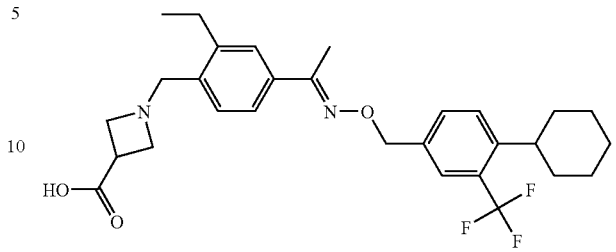

or a pharmaceutically acceptable salt, or a prodrug, or stereoisomer thereof.

2. A pharmaceutical composition comprising
   (i) a therapeutically effective amount of the compound of claim 1 or a pharmaceutically acceptable salt, or a prodrug, or stereoisomer thereof; and
   (ii) a pharmaceutically acceptable excipient.

* * * * *

UNITED STATES PATENT AND TRADEMARK OFFICE

(12)  CERTIFICATE EXTENDING PATENT TERM
UNDER 35 U.S.C. § 156

| | | | |
|---|---|---|---|
| (68) | PATENT NO. | : | 7,939,519 |
| (45) | ISSUED | : | May 10, 2011 |
| (75) | INVENTOR | : | Pan et al. |
| (73) | PATENT OWNER | : | Novartis AG |
| (95) | PRODUCT | : | MAYZENT® (siponimod) |

This is to certify that an application under 35 U.S.C. § 156 has been filed in the United States Patent and Trademark Office, requesting extension of the term of U.S. Patent No. 7,939,519 based upon the regulatory review of the product MAYZENT® (siponimod) by the Food and Drug Administration. According to United States Patent and Trademark Office records, the original expiration date of the patent as of the date of issuance of this certificate is May 19, 2024. Because it appears that the requirements of the law have been met, this certificate extends the term of the patent for the period of

(94)  1,561 days subject to the payment of maintenance fees as provided by law, with all rights pertaining thereto as provided by 35 U.S.C. § 156.

I have caused the seal of the United States Patent and Trademark Office to be affixed this 15th day of June 2022.

Kathi Vidal
_____
Katherine K. Vidal
Under Secretary of Commerce for Intellectual Property and Director of the United States Patent and Trademark Office